US012508140B2

(12) United States Patent
Mitchell et al.

(10) Patent No.: US 12,508,140 B2
(45) Date of Patent: Dec. 30, 2025

(54) ORTHOTIC BRACE AND CLIP ATTACHMENT MECHANISM AND ORTHOTIC SPRING TENSIONER

(71) Applicant: MD Orthopaedics, Inc., Wayland, IA (US)

(72) Inventors: Lucas J. Mitchell, Wayland, IA (US); Marcus William Powell, New London, IA (US); Shawn Edward Twyman, Mt. Pleasant, IA (US)

(73) Assignee: MD Orthopaedics, Inc., Wayland, IA (US)

( * ) Notice: Subject to any disclaimer, the term of this patent is extended or adjusted under 35 U.S.C. 154(b) by 0 days.

(21) Appl. No.: 18/714,833

(22) PCT Filed: Nov. 30, 2022

(86) PCT No.: PCT/US2022/051443

§ 371 (c)(1),
(2) Date: May 30, 2024

(87) PCT Pub. No.: WO2023/102072

PCT Pub. Date: Jun. 8, 2023

(65) Prior Publication Data

US 2025/0041091 A1 Feb. 6, 2025

Related U.S. Application Data

(60) Provisional application No. 63/340,206, filed on May 10, 2022, provisional application No. 63/284,416, (Continued)

(51) Int. Cl.
*A61F 5/01* (2006.01)

(52) U.S. Cl.
CPC ..... *A61F 5/0116* (2013.01); *A61F 2005/0197* (2013.01)

(58) Field of Classification Search
CPC .... A61F 5/0193; A61F 5/0116; A61F 5/0127; A61F 5/0111; A61F 5/0113;
(Continued)

(56) References Cited

U.S. PATENT DOCUMENTS 3,777,747 A * 12/1973 Friedman .............. A61F 5/0193 602/24
4,088,129 A * 5/1978 DiGiulio ............. F16C 11/0661 602/23

(Continued)

*Primary Examiner* — Kari K Rodriquez
(74) *Attorney, Agent, or Firm* — Gerald W. Roberts; John V. Daniluck; Dentons Bingham Greenebaum LLP

(57) ABSTRACT

A reversible tensioning device for an orthotic that includes: a cover; an insert rotatably disposed within the cover; a slot within the cover; a peg fixedly disposed on the insert and slidably located within the slot on the cover, the peg configured to slide between a first end portion and a second end portion of the slot; a spring fixedly attached to the cover and the insert and configured to urge the cover and the insert in opposite rotational directions; a first flange surface on the cover; and a second flange surface on the insert and facing an opposite direction from the first raised surface. The first flange surface and the second flange surface are configured to operably couple with third and fourth flange surfaces on an orthotic device to provide opposing forces on the reversible tensioning device.

12 Claims, 21 Drawing Sheets

Related U.S. Application Data filed on Nov. 30, 2021, provisional application No. 63/284,411, filed on Nov. 30, 2021.

(58) Field of Classification Search

CPC .... A61F 5/3753; A61F 5/3715; A61F 5/0123; A61F 2005/0179; A61F 2005/0165; A61F 2005/0132; A61F 2005/0197; A43B 13/28; A43B 13/30; A44B 11/2526; A44B 11/253; A44B 11/2584; A44B 11/2592; A44B 11/263; A44B 11/266

See application file for complete search history.

(56) References Cited

U.S. PATENT DOCUMENTS

| | | | | |
|---|---|---|---|---|
| 4,249,523 | A * | 2/1981 | Bidwell | A61F 5/0193<br>602/24 |
| 4,550,722 | A * | 11/1985 | Kurtz | A61F 5/0193<br>602/24 |
| 5,470,310 | A * | 11/1995 | Sutcliffe | A61F 5/0193<br>128/882 |
| 7,267,657 | B1 * | 9/2007 | Mitchell | A61F 5/0193<br>602/29 |
| 7,569,023 | B2 * | 8/2009 | Dobbs | A61F 5/0193<br>602/29 |
| 10,045,874 | B2 * | 8/2018 | Grosland | A43B 7/00 |
| 10,314,730 | B2 * | 6/2019 | Connolly | A61F 5/0116 |
| 2007/0073206 | A1 * | 3/2007 | Hatton | A61F 5/0193<br>602/5 |
| 2015/0335455 | A1 * | 11/2015 | Sorrenti | A61F 5/0123<br>602/16 |

* cited by examiner

ORTHOTIC BRACE AND CLIP ATTACHMENT MECHANISM AND ORTHOTIC SPRING TENSIONER

CROSS-REFERENCE TO RELATED APPLICATIONS

This application is an International Patent Application that claims priority to and incorporates by reference in their entireties each of the following: U.S. Provisional Application No. 63/284,411, filed on Nov. 30, 2021, entitled "UNITARY INJECTION MOLDED BAR FOR CORRECTING CLUBFOOT;" U.S. Provisional Application No. 63/284,416, filed on Nov. 30, 2021, entitled "REVERSIBLE AND SELF-CONTAINED TENSIONING DEVICE;" and U.S. Provisional Application No. 63/340,206, filed on May 10, 2022, entitled "ORTHOTIC BRACE AND CLIP ATTACHMENT MECHANISM WITH SPRING TENSIONER."

BACKGROUND

The present disclosure generally relates to devices used in connection with various orthotic devices. In particular, the disclosure relates to orthotic devices and related devices and systems used to implement the Ponseti method (also known as the Ponseti technique), which is a non-surgical technique that uses a series of casts, followed by an abduction brace, or ankle foot orthosis (AFO), to correct congenital clubfoot. Clubfoot causes a baby's feet to turn inward and downward; if not corrected, the child will be unable to walk or move properly.

Various orthoses are used for treatment of clubfoot. Most often, the orthosis is used as a holding device after correction by nonoperative or surgical methods. Typically, a more restrictive orthosis is used initially on a full-time schedule. Once the child begins to crawl and/or walk, different bracing regimens for daytime and sleeping can be prescribed.

SUMMARY

One aspect of the present disclosure includes a reversible tensioning device for an orthotic that includes: a cover; an insert rotatably disposed within the cover; a slot within the cover; a peg fixedly disposed on the insert and slidably located within the slot on the cover, the peg configured to slide between a first end portion and a second end portion of the slot; a spring fixedly attached to the cover and the insert and configured to urge the cover and the insert in opposite rotational directions; a first flange surface on the cover; and a second flange surface on the insert and facing an opposite direction from the first raised surface. The first flange surface and the second flange surface are configured to operably couple with third and fourth flange surfaces on an orthotic device to provide opposing forces on the reversible tensioning device.

Another aspect of the present disclosure includes an orthotic with a reversible tensioning device that includes: a bar having a bar torsion surface; a pair of shoe attachments each with a coupling having a shoe attachment torsion surface; a pair of reversible tensioners disposed between the bar and each of the pair of shoe attachments. Each of the reversible tensioners have: a tensioner cover having a tensioner cover torsion surface corresponding to one of the bar torsion surface and the shoe attachment torsion surface; an insert rotatably disposed within the tensioner cover between a first stop and a second stop, the insert having an insert torsion surface extending in a direction opposite the tensioner cover torsion surface and corresponding to the other of the bar torsion surface and the shoe attachment torsion surface; and a spring fixedly attached to the cover and the insert and configured to rotatably urge the insert toward the first stop.

Yet another aspect of the present disclosure includes an orthotic with a reversible tensioning device that includes: an elongated bar having right and left ends, and a pair of anti-rotation holes, each of the pair of anti-rotation holes located at one of the right and left end of the elongated bar; a pair of shoe attachments disposed on right and left ends of the elongated bar, each of the pair of shoe attachments comprising a cup with an anti-rotation flange; a pair of reversible tensioners disposed between the elongated bar and each of the pair of shoe attachments. Each of the reversible tensioners typically includes: a cover having an anti-rotation flange; an insert rotatably disposed within the cover between a first stop and a second stop, the insert having an anti-rotation flange extending in a direction opposite the cover anti-rotation flange; and a spring fixedly attached to the cover and the insert and configured to rotatably urge the insert toward the first stop.

Another aspect of the present disclosure is generally directed to an orthotic tensioning device and/or an orthotic system using the orthotic tensioning device such as an orthotic system for treating clubfoot using the Ponseti method using an orthotic tensioning device of the present disclosure. One such tensioning device typically includes a top insert having a cap portion with a top surface and a spring facing surface where the top surface has a bar aperture engaging projection and the spring facing surface has an elongated projection extending therefrom with an elongated portion spring receiving groove in a side of the elongated projection that receives an elongated projection engaging end of a spring; a bottom cap portion having at least one wall extending upward from a base portion and where the base portion has an interior facing side and an exterior facing side and where the interior facing side has an upward extending portion with an upwardly extending portion groove therein that receives an upwardly extending portion engaging end of the spring and retains the upwardly extending portion engaging end of the spring within the upwardly extending portion groove and where the exterior facing side of the bottom cap portion has an aperture therein that extends through to the interior facing side such that a distal end of the elongated projection extends through from the interior facing side and past the exterior facing side; and a retainer engaged to an outside surface of a portion of the elongated projection that extends through the base portion when the top insert is engaged with the bottom cap portion These and other aspects, objects, and features of the present disclosure will be understood and appreciated by those skilled in the art upon studying the following specification, claims, and appended drawings.

DETAILED DESCRIPTION

Figure 1:
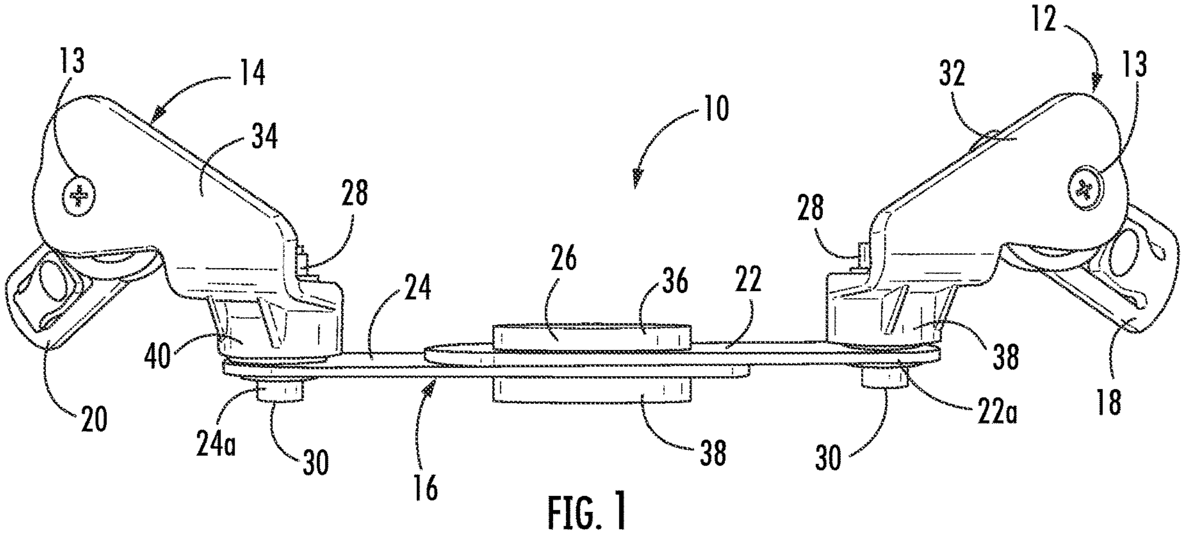
FIG. 1 is a front perspective view of a self-contained tensioning device engaged with and part of an orthotic brace device/system.

For purposes of description herein, the terms "upper," "lower," "right," "left," "rear," "front," "vertical," "horizontal," and derivatives thereof shall relate to the disclosure as oriented in FIG. 1. However, it is to be understood that the disclosure may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

FIG. 1 shows a foot abduction apparatus 10. The foot abduction apparatus 10 includes a left shoe connection assembly 12, a right shoe connection assembly 14, and an elongated member 16. The elongated member 16, an orthotic bar, holds the left shoe connection assembly 12 and the right shoe connection assembly 14 separated at a predetermined distance, which in turn holds the user's shoes and feet at the proper distance apart from one another according to the user's specific treatment of clubfoot.

The user's left shoe includes an attachment slot in the sole of an orthotic shoe that corresponds to and slides into engagement with the left foot attachment bracket 18 such that the orthotic shoe is removeable from engagement with the bracket 18 by hand and without the use of tools. Similarly, the user's right shoe sole includes an attachment slot that corresponds to and attaches to the left foot attachment bracket 20. The left foot attachment bracket 18 and the right foot attachment bracket 20 are each typically engaged with the spring arms 32, 34 using a screw 13 (see FIG. 1) or other fastener that engages an aperture in the plates 32, 34 that have circumferential ridges and/or grooves surrounding the aperture. The elongated member 16 includes first bar 22 and second bar 24 that are connected by a locking assembly 26. The locking assembly 26 receives the first bar 22 and the second bar 24 and holds them in place such that the ends 22*a*, 24*a* of bars 22, 24 are held at the proper, typically variable but predetermined, distance for a user and the user's specific clubfoot treatment.

The first bar 22 and the second bar 24 each typically include a slot 40. The locking assembly 26 may include a top portion 36 and a lower portion 38 that fit together to form the locking assembly 26 and are typically held in engagement with one another using a single locking fastener or screw; however, two or more fasteners, typically screws may also be used to hold the top portion 36 and lower portion 38 in engagement with one another. The top portion 36 and the lower portion 38 fit together with internal ribs (not shown) that fit within the slots 40 in the first bar 22 and the second bar 24. The internal ribbing allows the first bar 22 and the second bar 24 to slide over one another to lengthen and shorten the elongated bar 16 as necessary to appropriately be used by a user of different age/size. The internal ribbing also prevents the first bar 22 and the second bar 24 from rotating with respect to one another adding strength to the assembly.

Figure 2:
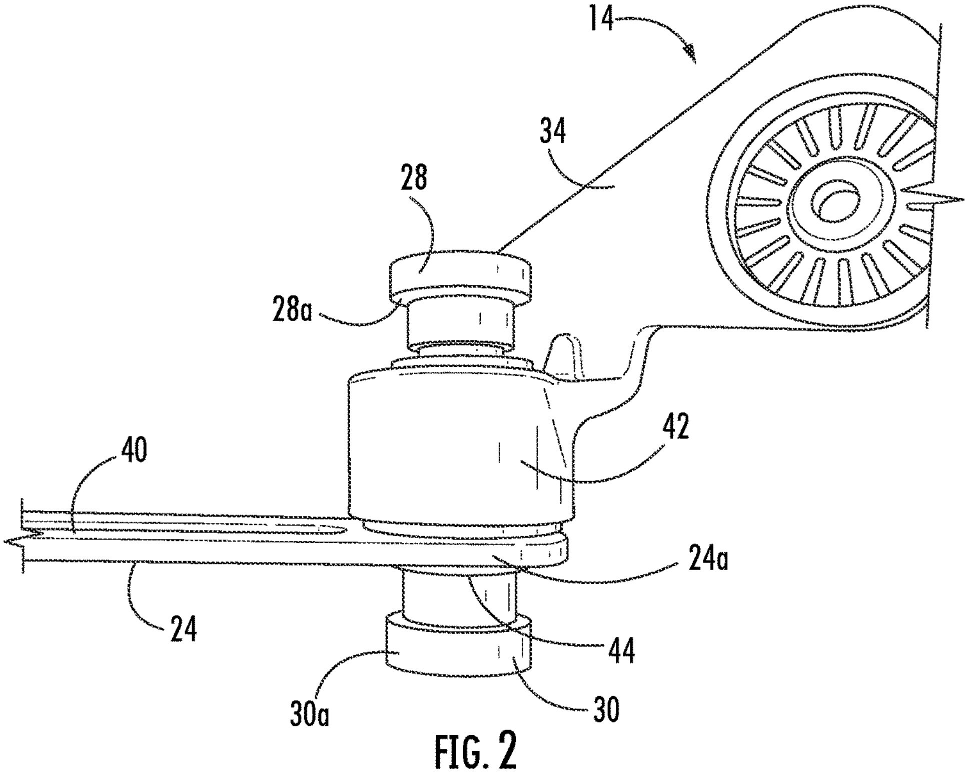
FIG. 2 is an enlarged view of a self-contained tensioning device.

As shown in FIG. 2, the right shoe connection assembly 14 includes a spring arm 34 and fasteners 28, 30. The left shoe connection assembly similarly includes a spring arm 34 with fasteners 28, 30. In an embodiment, the fastener 28 is a bolt with a finger-tightenable head 28*a* such that the fastener 28 may be engaged by hand and without the use of tools. The bolt 28 feeds through the cup 42 of the spring arm 34, through an anti-rotation hole 48 in second bar 24, and through the through-hole 56 of the reversible tensioning device 50 (see FIG. 3) that is within the cup 42. The bolt 28 is tightened by fastener 30 which may be a nut with a hand-tightenable head 30*a*. It should be known that the bolt 28 and nut 30 may be reversed without deviating from the scope of the disclosure.

When the plate 34 with the reversible tensioning device 50 is located where the practitioner desires based on the treatment, the nut 30 is tightened down on the bolt 28 holding the right shoe connection assembly 14 in the proper orientation or angle for the desired treatment. Similarly, the left shoe connection assembly 12 includes all of the same elements. The spring arm 32 on the left side may be a mirror image of the spring arm 34 as shown in FIG. 2. For ease of assembly, in an embodiment of the present disclosure, the fasteners 28, 30 and the tensioning device 50 (as described in more detail below) may be interchangeable between the right and left sides.

Figure 3:
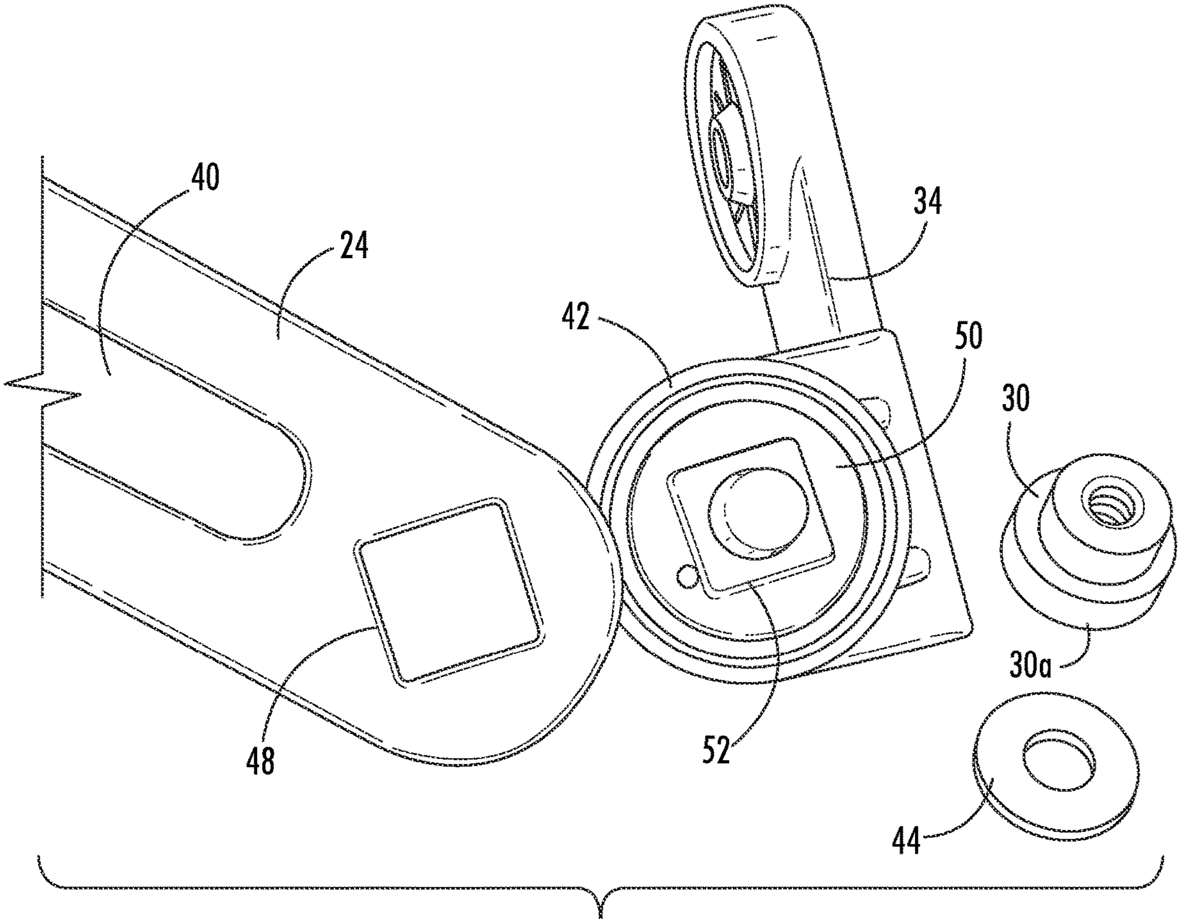
FIG. 3 is a tensioning device of the present disclosure disengaged from the orthotic brace device/bar system of the present disclosure.

As shown in FIG. 3, the tensioning device 50 includes a raised flange 52 that corresponds to the anti-rotation hole 48 in the second bar 24. When the right shoe connection assembly 14 is assembled, the raised flange 52 on the tensioning device 50 fits within the anti-rotation hole 48 in the second bar, and at least that portion of the tensioning device 50 is prevented from rotating. While the raised flange 52 and the anti-rotation hole 48 are shown as squares, they could be triangular, star-shaped, or any other shape known in the art that prevents relative rotation between the two parts 52, 48. Additionally, the shapes of the flange 52 and the anti-rotation hole 48 do not need to match, as long as there is at least one portion of each that meet and prevent relative rotation.

Figure 4:
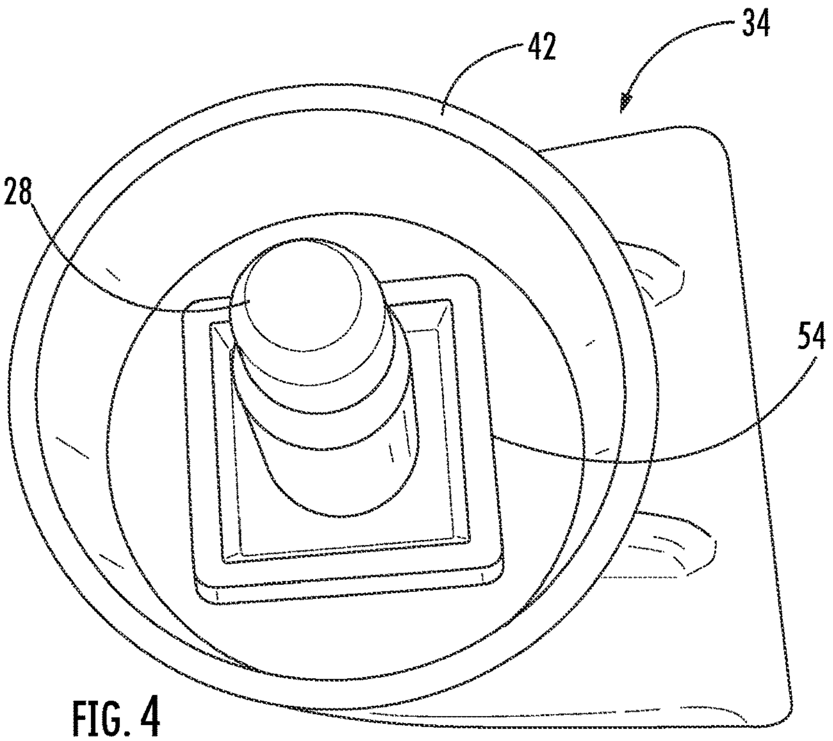
FIG. 4 is a top interior view of a tensioning device of the present disclosure.

As shown in FIG. 4, the cup 42 of the spring arm 34 includes an anti-rotation flange 54 at the base of the interior of the cup. When the right shoe connection assembly 14 is assembled, a second raised flange 52 on the opposite side of the reversible tensioning device 50 fits within the anti-rotation flange 54 in the cup 42 of the spring arm 34, at least that portion of the reversible tensioning device 50 is prevented from rotating. While the raised flange 52 and the anti-rotation flange 54 are shown as squares, they could be triangular, star-shaped, or any other shape known in the art that prevents relative rotation between the two parts 52, 48. Additionally, the shapes of the flange 52 and the anti-rotation flange 54 do not need to match, as long as there is at least one portion of each that meet and prevent relative rotation.

Figure 6:
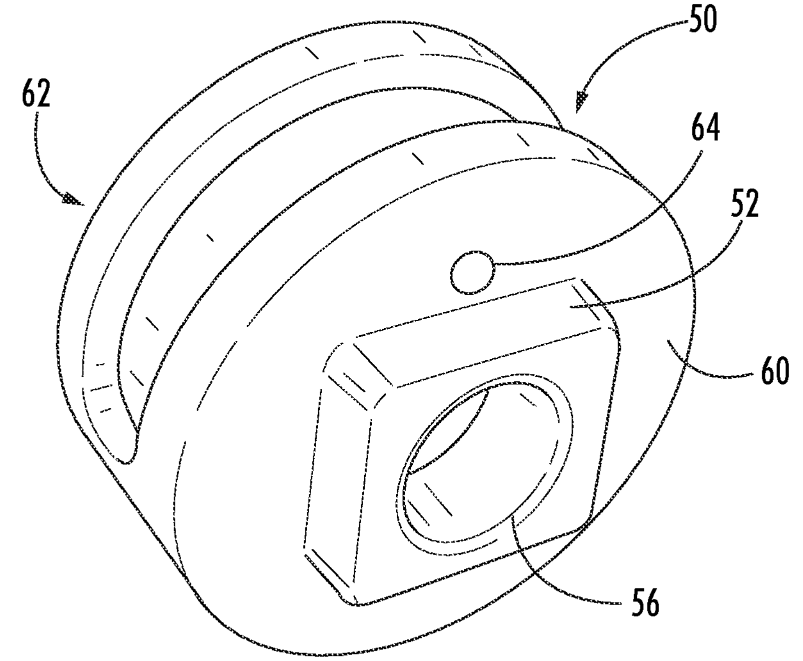
FIG. 6 is a front perspective view of a tensioning device of the present disclosure.
Figure 7:
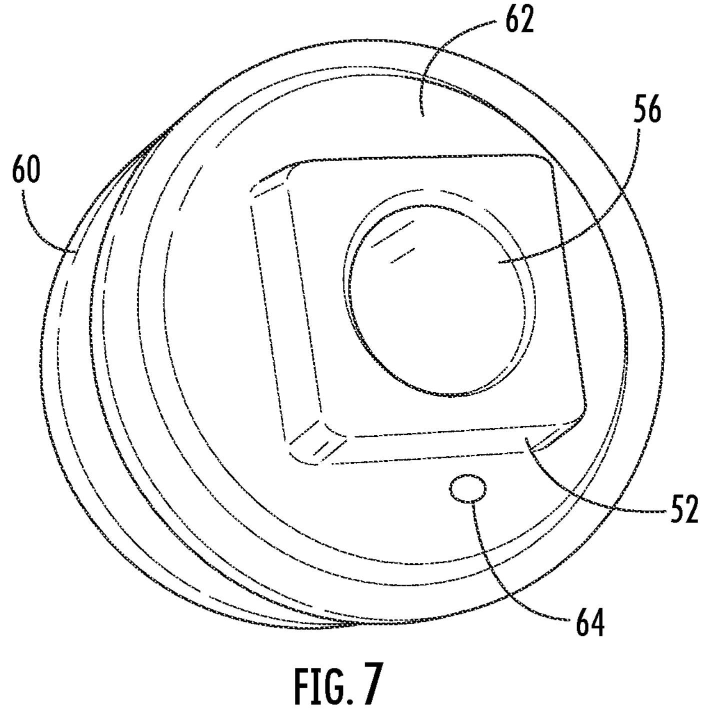
FIG. 7 is a front perspective view of a tensioning device of the present disclosure.

As described in more detail below, the right shoe connection assembly 14 and the second bar 24 may be allowed to rotate relative to one another because of the internal rotation allowed between the portions 60, 62 (see FIGS. 6 and 7) of the tensioning device 50.

The tensioning device 50 is designed to provide rotational tension or rotational force between two elements. In an embodiment, those two elements are the elongated bar 16 and the right and left shoe connection assemblies 12, 14. This allows for some rotation by a user when wearing the orthotic while providing the rotational force to urge the foot back into the preferred position for treatment when the foot is at rest. In order to reverse the tensioning rotational direction, the provider or the user may simply flip the reversible tensioning device 50 over, flipping the direction of the spring force.

As shown in FIGS. 5-8, the tensioning device 50, which may be a reversible tensioning device, includes a cover 60, an insert 62, and a spring 72. The insert 62 may be rotatably nested within the cover 60. In this embodiment, rotatably nested typically means that the insert 62 fits within the cover 60 while retaining the ability to rotate freely within it. Each of the cover 60 and the insert 62 includes a spring locator 64. In an embodiment, the spring 72 is a round metal spring with locator arms 70 on each end of the spring 72 pointing substantially parallel or parallel to the axis of the spring. The spring locator 64 is a hole that the spring locator arms 70 are fixed within, in at least the embodiment of FIGS. 5-8, an interference or friction fit.

The cover 60 of the tensioning device 50 may include a rotation-limiting slot 68. The insert 62 may include a rotation-limiting peg 66. As the insert 62 rotates within the cover 60, the peg 66 slides within the slot 68. The slot 68 defines the rotational movement allowed by the tensioning device 50, and by extension the rotational movement allowed between the each of the right and left shoe connection assemblies 12, 14 and the elongated bar 16.

Figure 5:
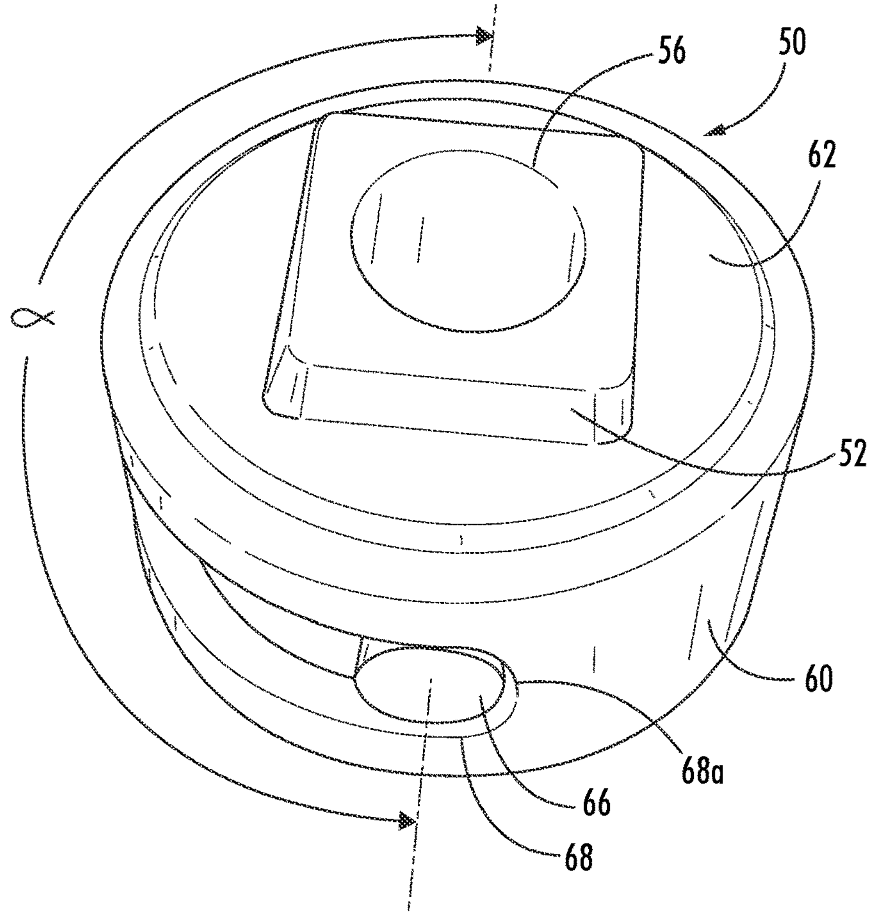
FIG. 5 is a perspective view of a tensioning device of the present disclosure.

In this way, a practitioner may set the allowable rotational movement by a foot of a user in their treatment. As shown in FIG. 5, the angle ox is shown as 180 degrees, but it should be known that this angle could be any angle desired by the practitioner. However, a 180-degree angle could be a high limit as it would be difficult for a user to turn their foot any more than that amount.

The tensioning device 50 includes anti-rotation features 52 on both the cover 60 and the insert 62. The anti-rotation features 52 as shown are raised flanges that correspond to the anti-rotation hole 48 within the elongated bar 16 and the anti-rotation flange 54 within the cup 42 of the spring arm 34.

Figure 8:
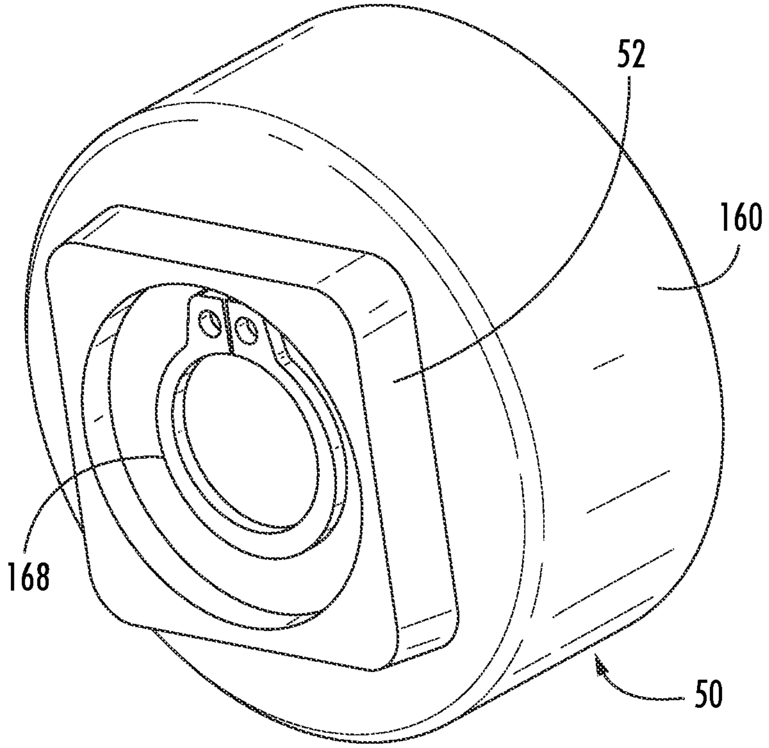
FIG. 8 is a rear perspective view of a tensioning device of another embodiment of the present disclosure.
Figure 9:
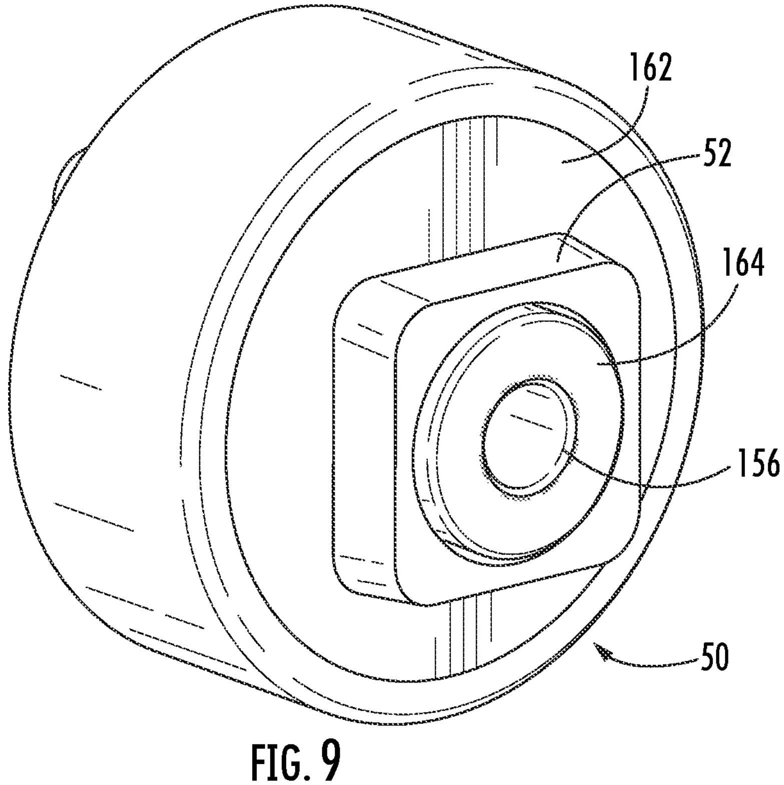
FIG. 9 is a front perspective view of the tensioning device shown in FIG. 8.
Figure 10:
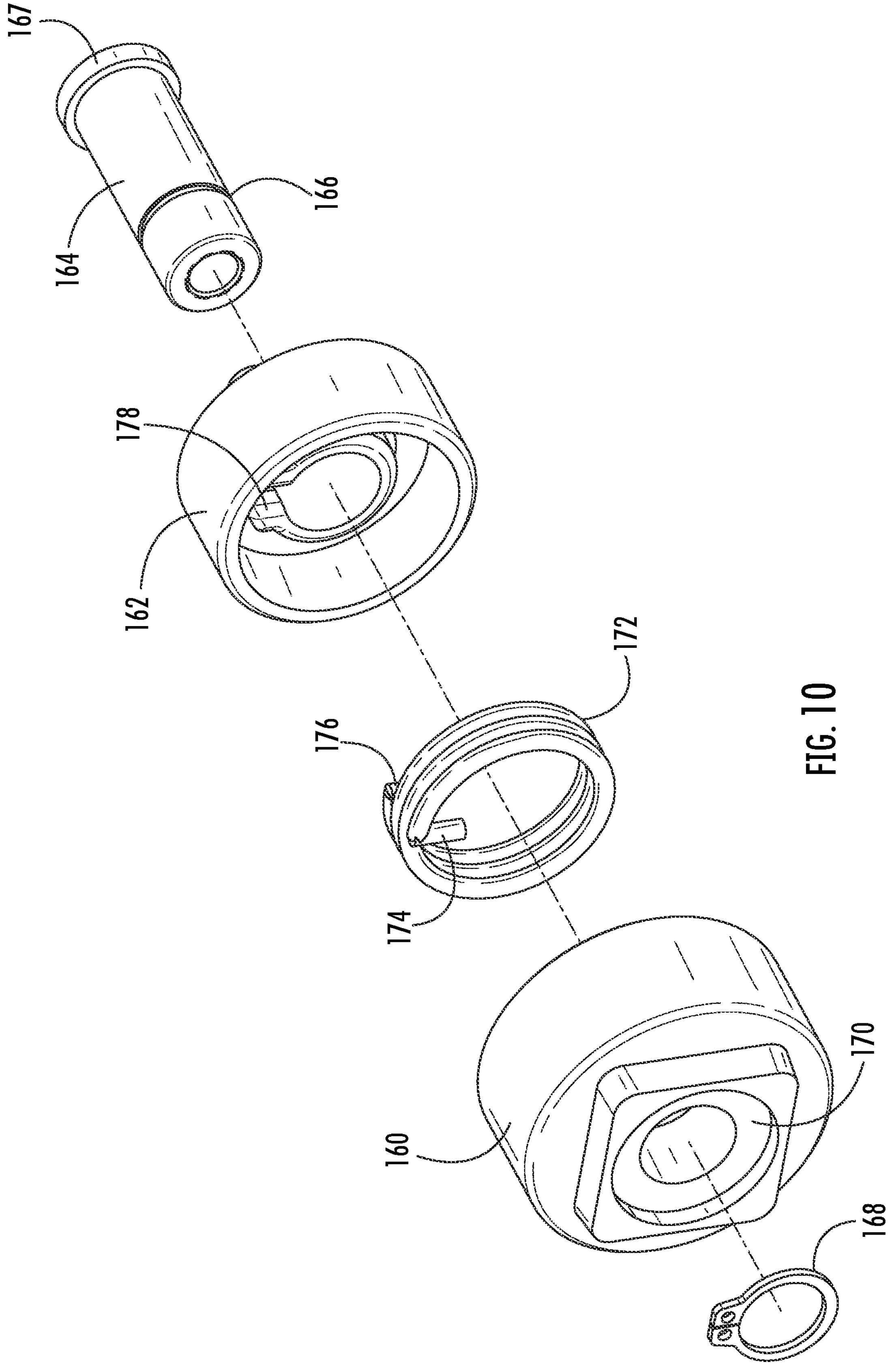
FIG. 10 is an exploded view of the tensioning device shown in FIG. 8.
Figure 11:
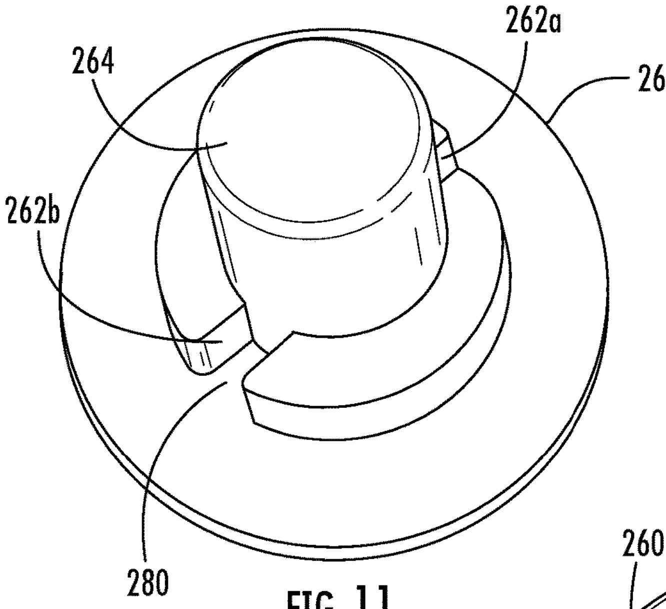
FIG. 11 is a perspective view of an inner insert housing of a tensioning device according to an aspect of the disclosure.

In another aspect of the present disclosure, as shown in FIGS. 8-10, the spring tensioner 150 may be held together by a hollow pin 164 between the cover 160 and the insert 162. The cover 160, the insert 162, and the spring 172 work similarly to the above detailed embodiment, but it does not have a rotation-limiting peg 66 nor the slot 68. Instead, the tensioning device 150 may include a hollow pin 164 with a head 167 and a groove 166. A retaining ring 168 may be used.

The spring 172 may include a first offshoot 174 that fits within a groove 174 and a second offshoot 176 on either end of the spring 172. The first offshoot 174 fits within a groove 178 on the inside of the insert 162, and the second offshoot fits within a groove 180 on the inside of the cover 160. The groove and offshoot configurations prevent relative movement of the offshoots 174, 176 and their respective grooves 178, 180, and provide the tension between the cover 160 and the insert 162 to allow rotational movement while urging the tensioning device 150 back to its default state.

The hollow pin 164 is inserted into the either the insert 162 or the cover 160, and the head sits within a depression 170 when inserted in the cover 160. On the other end of the pin 164, a spring clip 168 is snapped into the groove 166 of the hollow pin 164 and sits within the depression 170 on the other of the cover 160 or the insert 162. Using the hollow pin may offer more stability for the tensioner 150.

In still another embodiment, the pin 164 may be a solid pin without the hollow center portion, and may not include a groove 166. In this embodiment, the tensioning device may be held together by the squeezing force of the spring clip 168 against the shaft of the pin 164. It should be known that other fasteners may be used besides the spring clip 168 like a cotter pin or any other fastening device known in the art.

Preferably, the shapes of the anti-rotation features are the same, or at least similar enough such that the tensioning device may be flipped over and the anti-rotation features 52 may be used in both the anti-rotation hole 48 within the elongated bar 16 and the anti-rotation flange 54 within the cup 42 of the spring arm 34. While the raised flange 52 and the anti-rotation flange 54 are shown as squares, they could be triangular, star-shaped, or any other shape known in the art that prevents relative rotation between the two parts 52, 48. Additionally, the shapes of the flange 52 and the anti-rotation flange 54 do not need to match, as long as there is at least one portion of each that meet and prevent relative rotation.

When the tensioning device 50 is assembled, the cover 60, insert 62, and spring 72 are located together with the peg 66 urged against one end 68*a* of the slot 68 by the spring force. As the insert 62 and cover 60 are rotated relative to one another, the spring force acts against and applies a rotational force against this movement. When the force of rotation by the user is removed, the spring acts to urge the peg back against the end 68*a* of the slot 68. Because the spring force is applied in a single direction, it is simple movement to change the direction of rotational spring force. The tensioning device 50 may be a reversible tensioning device that may be simply flipped over, which also flips the direction of spring force. In this way, the same reversible tensioning device 50 may be used on both the right and left side. This allows a manufacturer to build and maintain tools for a single design without requiring right and left hand covers, inserts, and springs.

When the foot abduction device 10 is in use, the user's feet are set at the desired angle in an outward angle by the practitioner based on the treatment plan for the user. The reversible tensioning device allows the user to rotate their foot, while applying force to place the foot back in the desired position once the user removes the force of their foot.

Different users of the foot abduction apparatus 10 may require different spring tensions on the foot. To help the practitioner in selecting the proper reversible tensioning device 50, different colors may be used. For instance, in an embodiment as an example, the lightest tension may be a green device 50, a middle tension may be yellow, and the highest tension may be red. It should be known that there may be many different tensions available with many different colors. In this way, a practitioner may be able to quickly and easily select the proper tension for a given user based on their treatment plan. In another embodiment, a user may be given a set of reversible tensioning devices 50. The set may include multiple pairs of the reversible tensioning devices 50 that the user can easily swap out typically by hand and without the use of tools and also typically without the need for another visit to the practitioner.

In another embodiment as shown in FIGS. 11-26, a spring tensioner 250 includes an inner insert housing 262, an outer insert housing 260, a wind torsion spring 272, and an external retaining ring 268 (see FIGS. 11-14). In this embodiment, the pin 264 is integral with the inner insert housing 262 as opposed to a separate piece of the assembly.

Figure 12A:
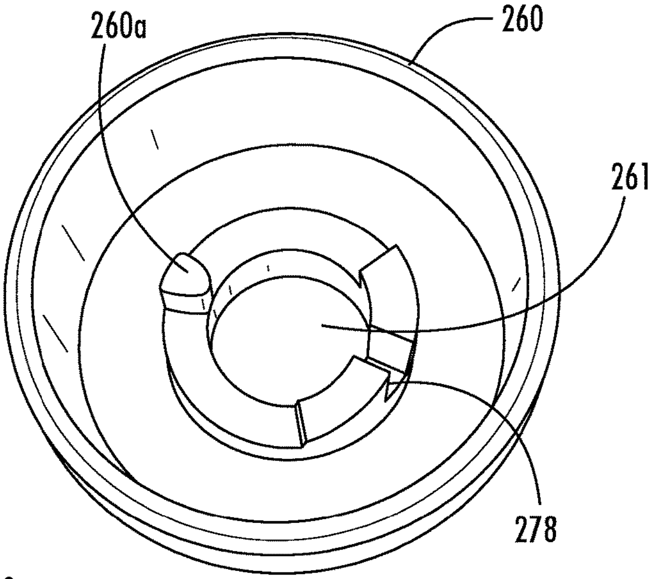
FIG. 12A is a perspective view of an outer insert housing of a tensioning device according to an aspect of the disclosure.
Figure 12B:
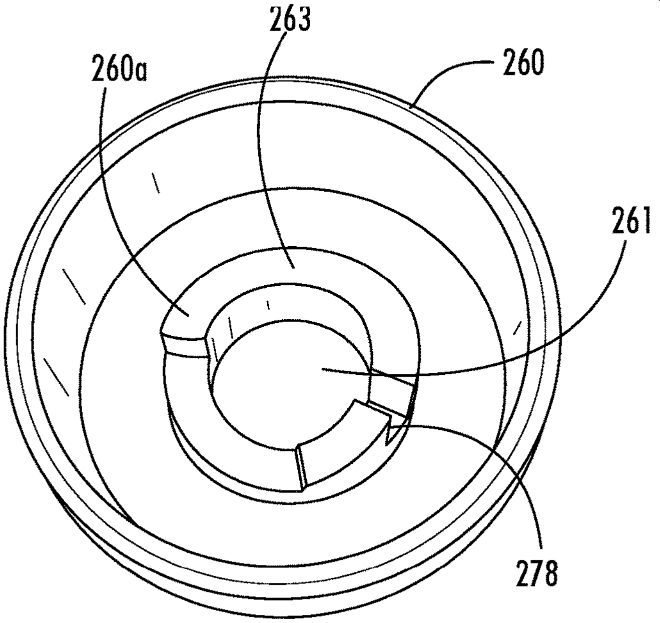
FIG. 12B is a perspective view of an outer insert housing of a tensioning device according to another aspect of the disclosure.
Figure 12C:
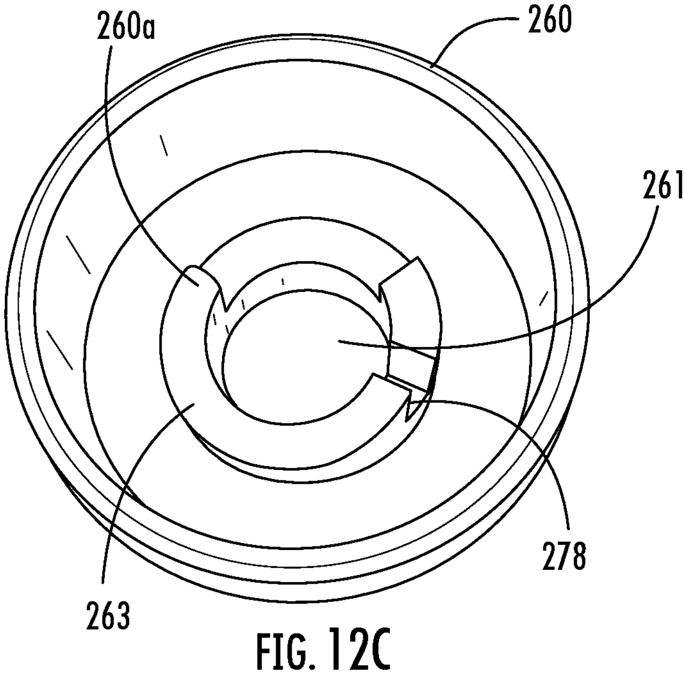
FIG. 12C is a perspective view of an outer insert housing of a tensioning device according to an aspect of the disclosure.
Figure 13:
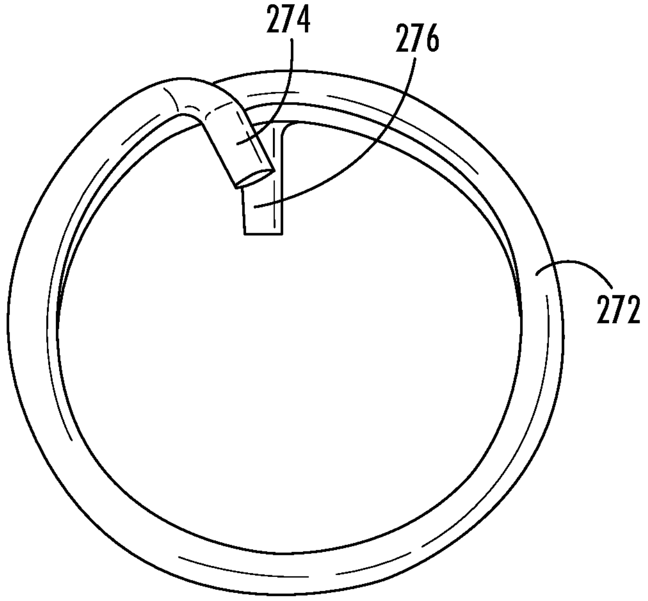
FIG. 13 is a perspective view of a torsion spring used in a tensioning device according to an aspect of the disclosure.
Figure 14:
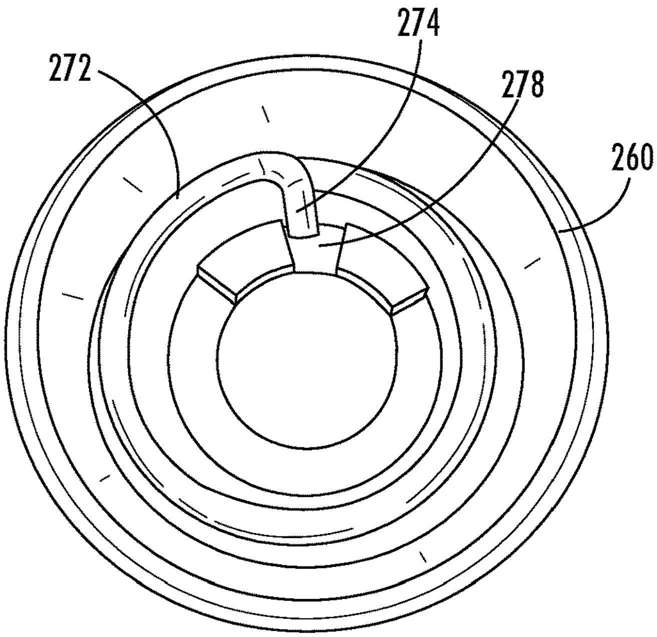
FIG. 14 is a top view of the torsion spring located in an outer insert housing of an aspect of the disclosure.
Figure 15:
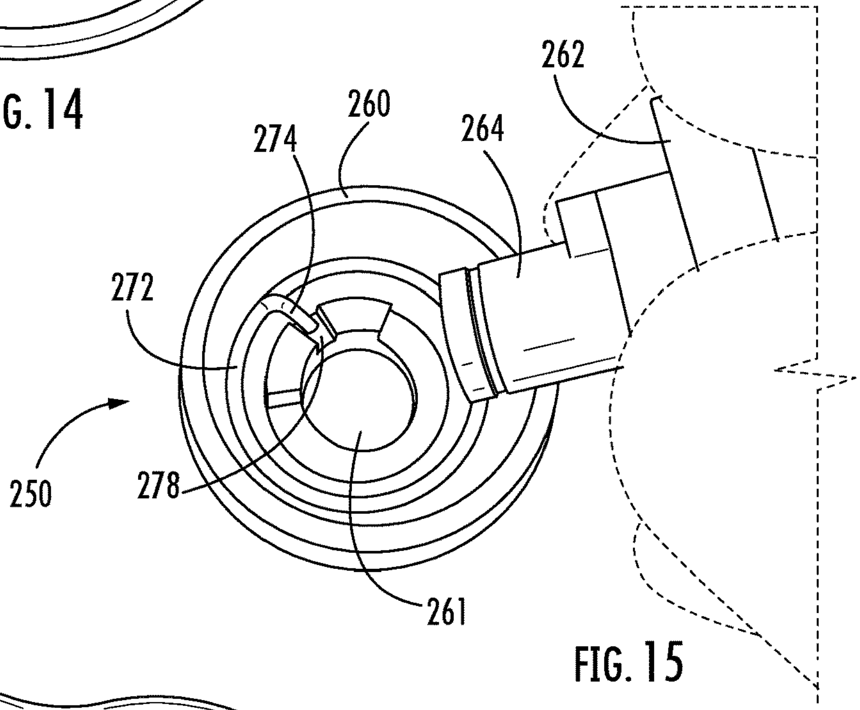
FIG. 15 is a top perspective view of the inner insert housing being inserted into the outer insert housing of an aspect of the disclosure.
Figure 16:
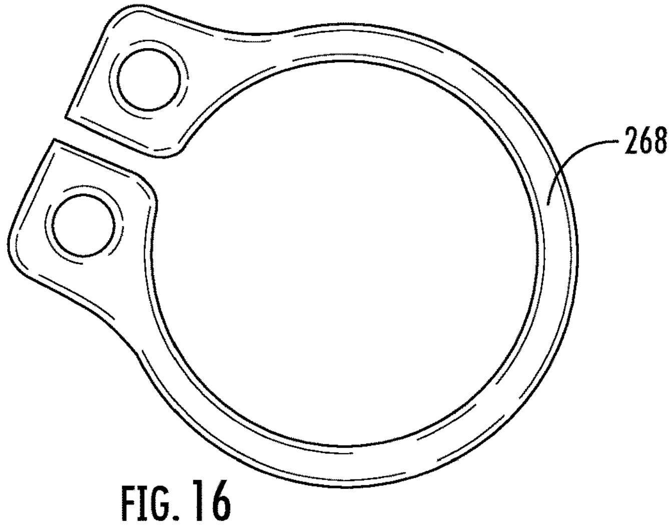
FIG. 16 is a top plan view of a retaining ring of an aspect of the disclosure.
Figure 17:
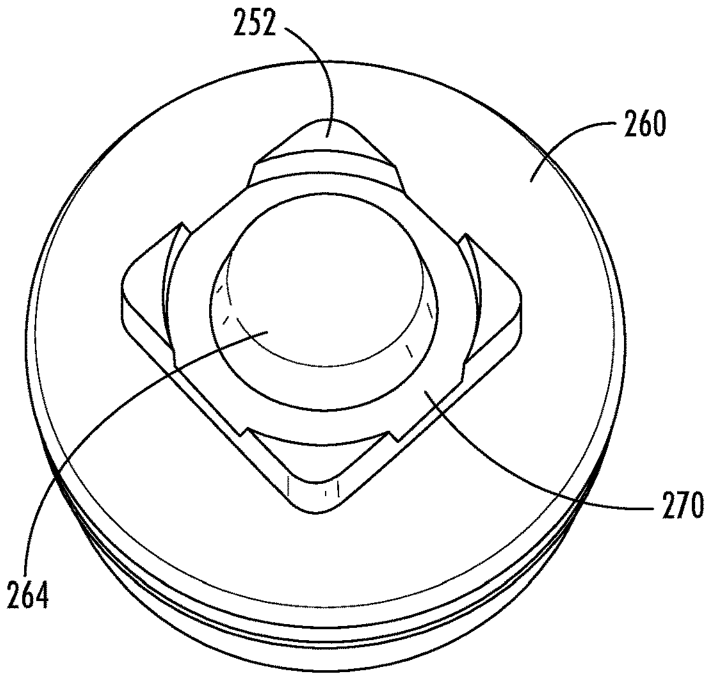
FIG. 17 is a bottom exterior view of the outer insert housing of a spring tensioner according to an aspect of the disclosure before the retaining ring is engaged thereto.
Figure 18:
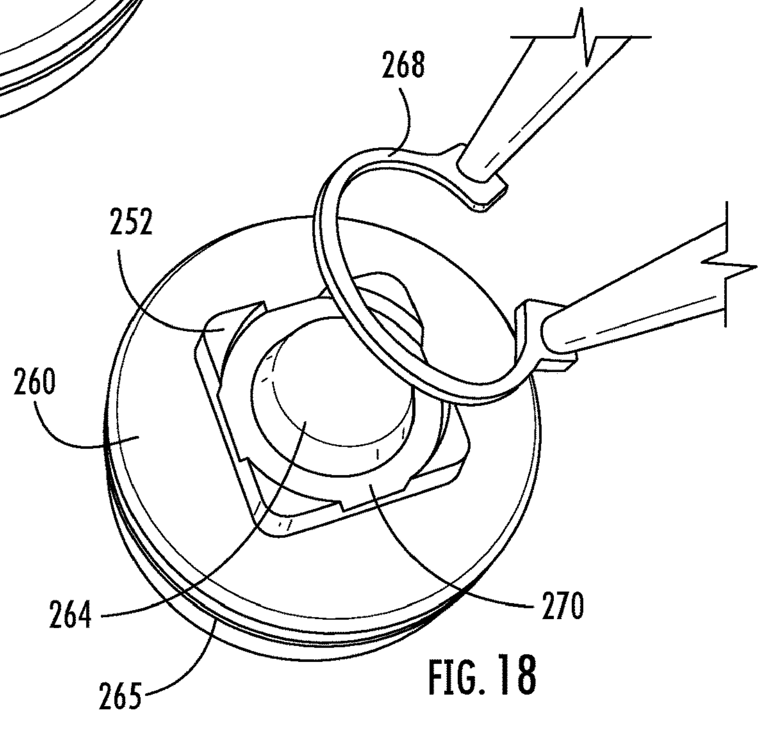
FIG. 18 is a bottom exterior perspective view of a retaining ring being assembled onto and into engagement with the spring tensioner assembly according to an aspect of the disclosure.
Figure 19:
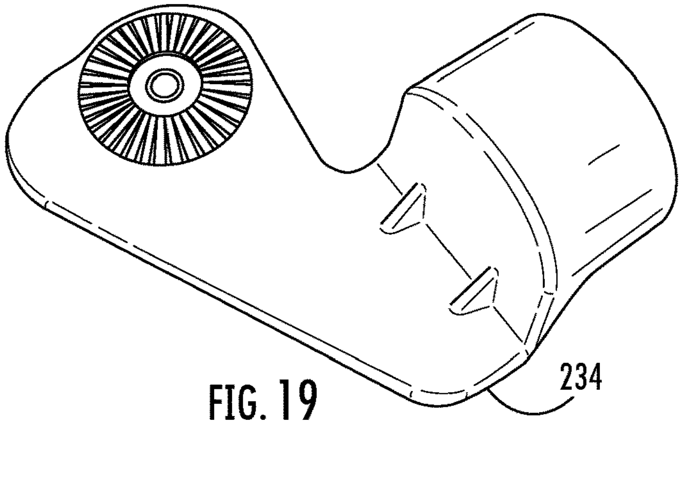
FIG. 19 is a perspective view of a left spring clip according to an aspect of the disclosure.
Figure 20:
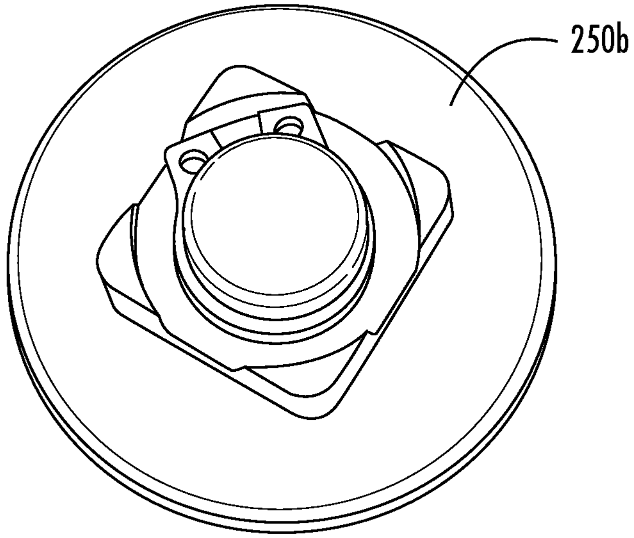
FIG. 20 is a bottom perspective view of a left spring tensioner according to an aspect of the disclosure.
Figure 21:
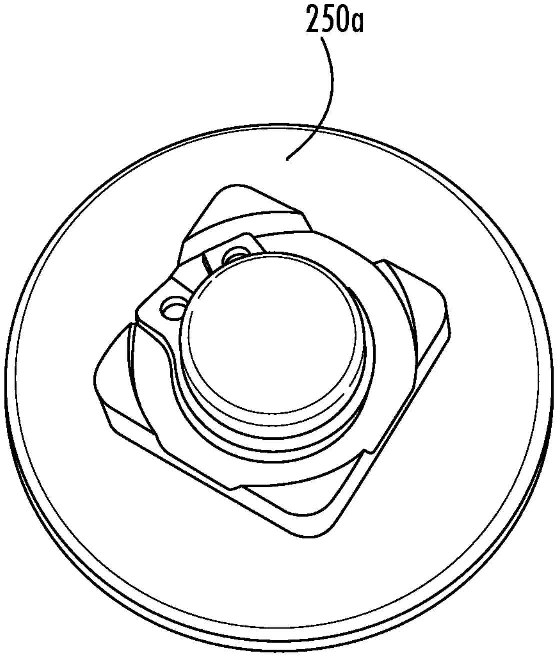
FIG. 21 is a bottom perspective view of a right spring tensioner according to an aspect of the disclosure.
Figure 22:
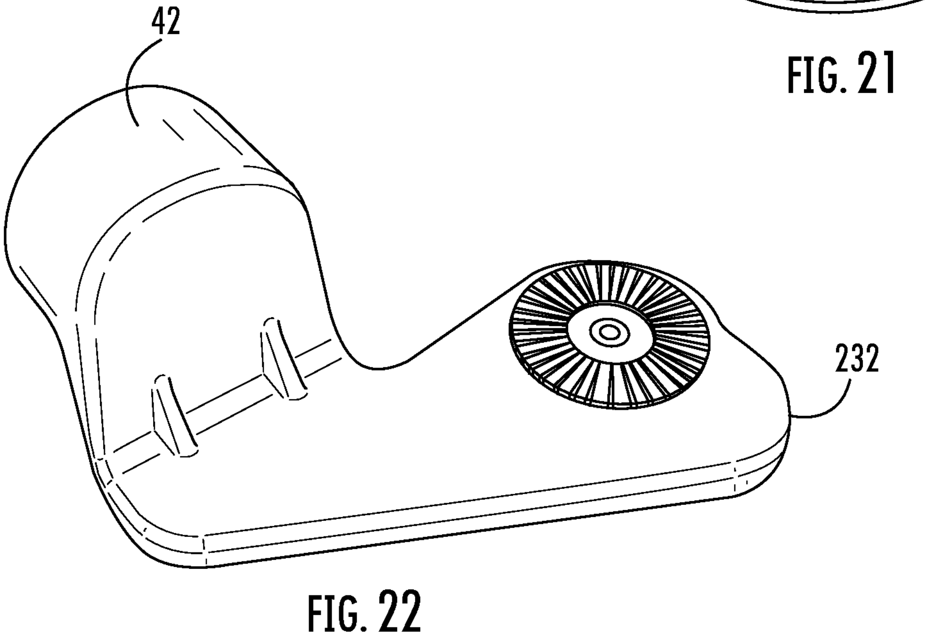
FIG. 22 is a perspective view of a right spring clip according to an aspect of the disclosure.
Figure 23:
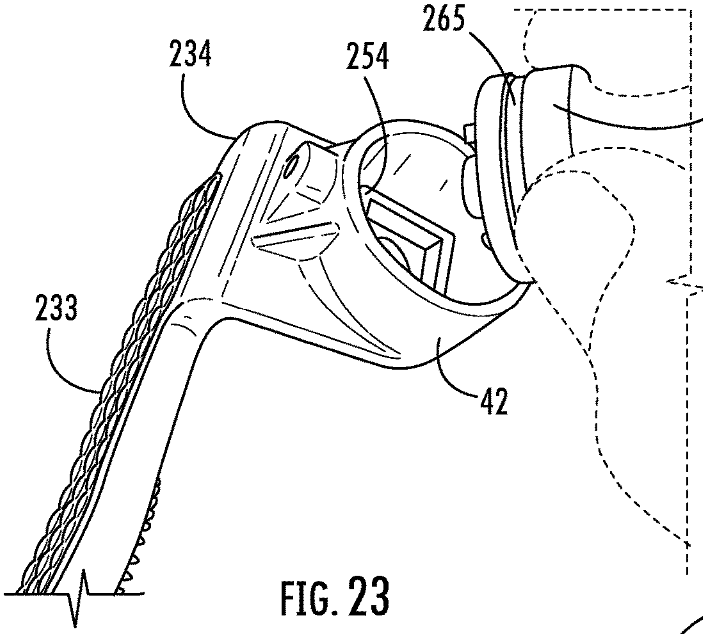
FIG. 23 is a perspective view of the left spring tensioner being inserted into the left spring clip according to an aspect of the disclosure.
Figure 24:
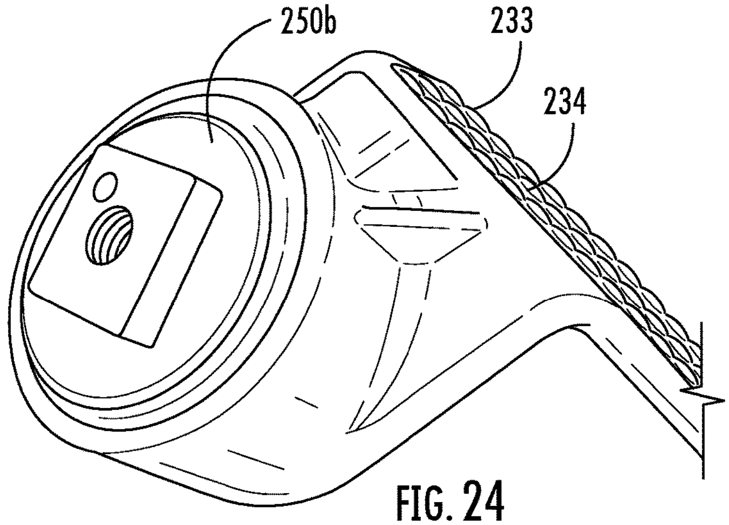
FIG. 24 is a perspective view of the left spring clip with the left spring tensioner inserted into the cup of the spring clip according to an aspect of the disclosure.

As shown in FIGS. 15-18, to assemble the spring tensioner 250, the wind torsion spring 272 is placed inside the outer insert housing 260 (see FIGS. 12A-12C). An offshoot 274 is aligned with a groove or a flange 278 within the interior of the outer insert housing 260 to prevent relative rotation of the end of the wind torsion spring 272 and the outer insert housing 260. The outer insert housing includes a boss 260*a* that preloads the spring 272, and acts as a rotational stop against bosses 262*a* and 262*b* of the inner insert housing 262 when assembled. Instead of a post for a boss a solid elevated portion 263 on one half or another of the interior mechanism within the interior of the outer insert housing 260 may be used (See FIGS. 12B and 12C). The portion proximate groove or flange 278 may be an inclined ramp upward toward the drop into the groove 278. The pin 264 of the inner insert housing 262 is placed within the center opening 261 of the outer insert housing 260 and a groove or a flange 280 is aligned with a second offshoot 276 of the wind torsion spring 272 to prevent relative rotation of the end of the wind torsion spring 274 and the inner insert housing 262.

With the insert housings 260, 262 sandwiched around and properly located with the wind torsion spring 272, the external retaining ring 268 may be placed within a depression 270 in the anti-rotation feature 252 on the outer insert housing 260. The external retaining ring 268 is fit within a groove 266 within the pin 264 of the inner insert housing 262 to prevent the insert housings 260, 262 from separating and holding the assembly of the reversible tensioning device together. In order to get clockwise or counter-clockwise motion and resistance, the spring tensioner 250 may be simply flipped. In other embodiments, right-hand and left-hand wind torsion springs 272 may be used either with standard or right-hand and left-hand insert housings 260, 262 in order to keep the same orientation of the tensioning devices on either side of the orthotic device 10.

Once the spring tensioner 250 is assembled, it may be placed into the interior of the cup 42 of the orthotic device 10. FIGS. 19-26 detail the second stage of the assembly of the orthotic device 10. In this stage, right and left spring tensioners 250*a* and 250*b* are placed in right and left spring arms 232 and 234, respectively. The right and left spring arms 232, 234 typically have integral cups 42 that are typically not removeable by hand and without the use of tools from engagement with the overall spring arm(s). The cup 42 typically surround the spring tensioner 250. Inside the cup 42 is a raised anti-rotation flange 254. The anti-rotation feature 252 on the spring tensioner 250 fits within the anti-rotation flange 254 of the right and left spring arms 232, 234, and prevents relative rotation between the spring tensioner outer insert housing 260 and the respective spring arm 232, 234. The right and left spring arms typically have a silicon, natural rubber, thermoplastic rubber, or a thermoplastic elastomer 233 applied to the non-fastener engaging side of the arms such that if a user were to stand using the orthotic systems of the present disclosure they would be less likely to slip and fall. The silicon, rubber, thermoplastic rubber, or thermoplastic elastomer may be textured with bumps or grooves for better friction resistance. The thermoplastic elastomer conceivably may be a styrenic block copolymer, a thermoplastic polyolefin elastomer, a thermoplastic vulcanizate, a thermoplastic polyurethane, a thermoplastic copolyester, a thermoplastic polyamide, and combinations of one or more of the above types of elastomers. Any component with Shore A hardness of zero (0) to one hundred (100) could be used in the context of the present disclosure.

Figure 25:
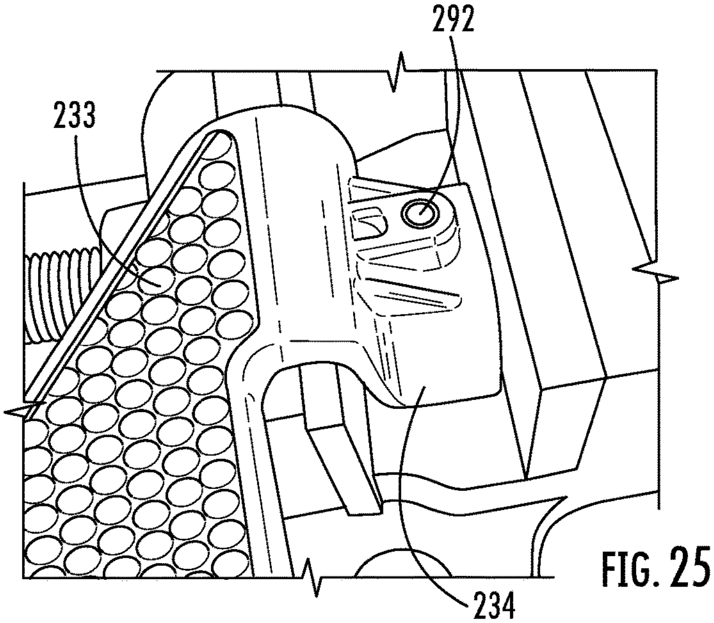
FIG. 25 is a view of the spring tensioner being clamped into the cup of the spring clip according to an aspect of the disclosure.
Figure 26:
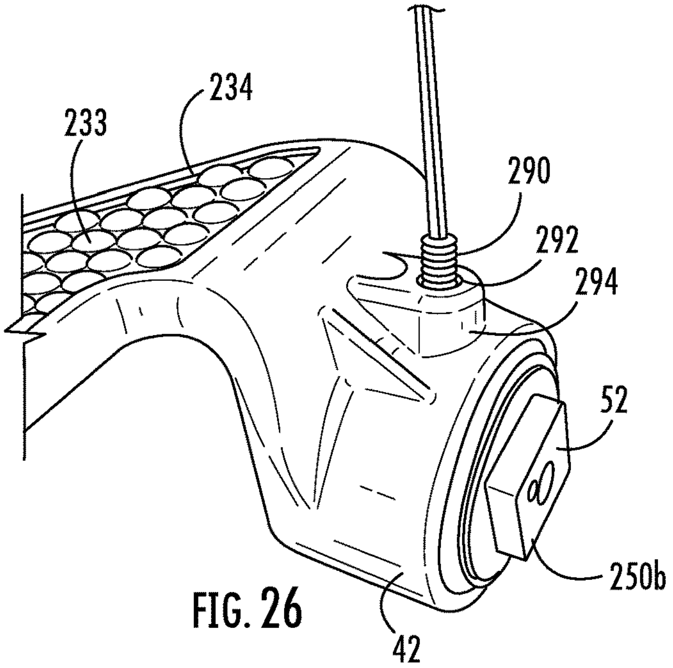
FIG. 26 is a view showing a hex wrench tightening in a set screw to hold the spring tensioner within a spring clip of an aspect of the disclosure.

The spring tensioner 250 then may be clamped (an external workbench mounted vise is shown in FIG. 25, but the clamp could be any clamp known in the art) to ensure that the spring tensioners 250*a* 250*b* are seated completely within the respective spring arms 232, 234. As shown in FIG. 26, a set screw 290 may then be inserted into a threaded insert 292 in a boss 294 on a side of the cup 42 of each of the spring arms 232, 234. The set screw 290 may be tightened down within a groove 265 on a side of the outer insert housing 260 of the spring tensioner 250 to hold it in place. The fastener 290 may be countersunk into the cup 42 of the spring clips 232, 234 as shown with the hex head such that it is unreachable by the user to remove without a hex wrench that can reach into the countersink. It should be known that other attachment methods may be implemented without deviating from the spirit of the disclosure. For instance, the spring arm may be overmolded over the spring tensioner, an undercut may be molded into the spring arm and used to hold the spring tensioner in place, a barb may be machined onto the spring tensioner that holds the spring tensioner within the cup of the spring arm, or any other attachment known in the art.

Figure 27:
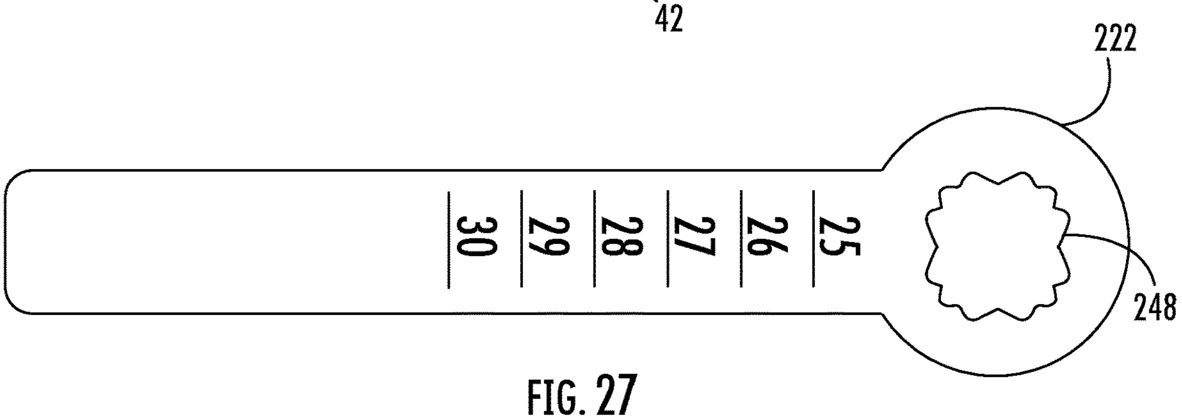
FIG. 27 is a top plan view of a bar of an aspect of the disclosure.
Figure 28:
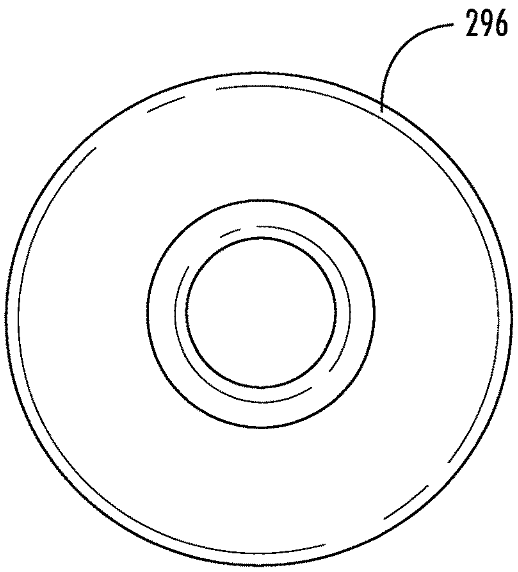
FIG. 28 is a top view of a washer for the fourth stage assembly of the orthotic device according to an aspect of the disclosure.
Figure 29:
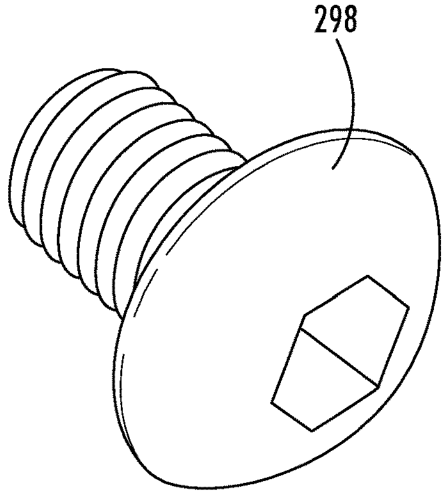
FIG. 29 is a perspective view of a fastener for the fourth stage assembly of the orthotic device according to an aspect of the disclosure.
Figure 30:
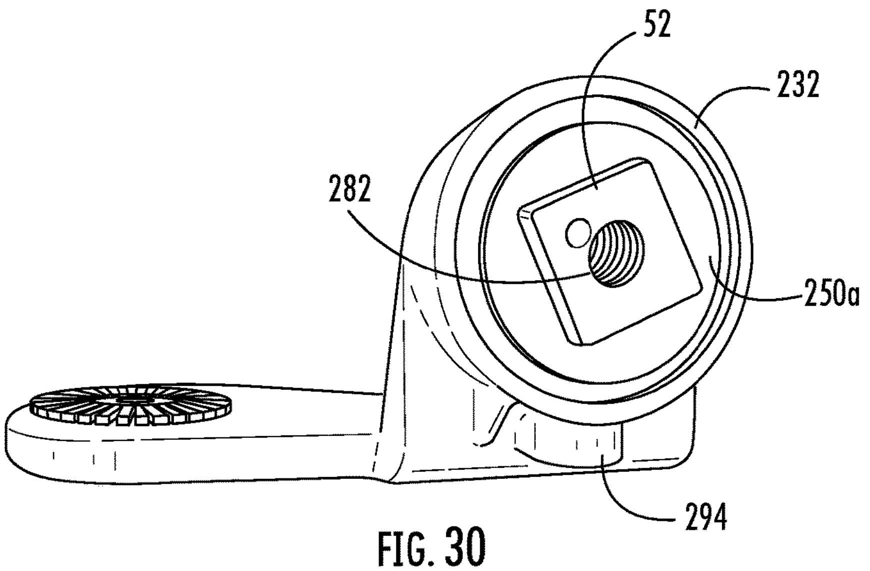
FIG. 30 is a side perspective view showing the attachment threaded hole in a spring tensioner according to an aspect of the disclosure.

With the spring tensioners 250*a* and 250*b* seated within the respective spring arms 232, 234, the spring arms may then be attached to the first and second bars 222, 224 in the third stage of assembly shown in FIGS. 27-34. For ease of disclosure, shown in FIG. 27 is the right bar 222 and in FIG. 30 is the right spring arm 232, but it should be known that the same assembly process is done for the left spring arm 234 and the left bar 224. The right bar 222 may include an anti-rotation hole 248.

Figure 31A:
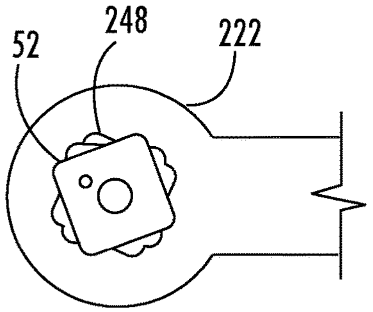
FIGS. 31A-31C are top plan cutaway views of different positions the spring clip may be attached to the bar according to an aspect of the disclosure.
Figure 31B:
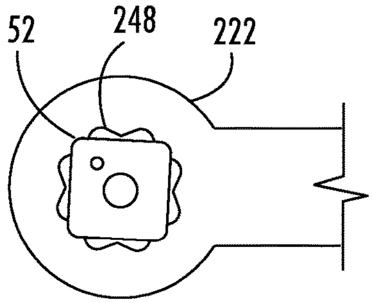
Figure 31C:
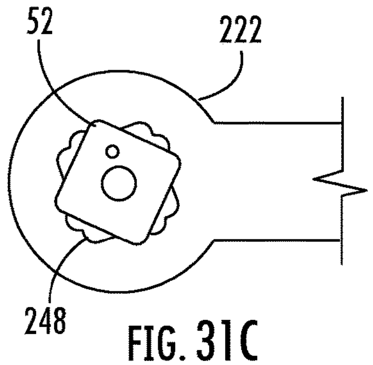
Figure 32:
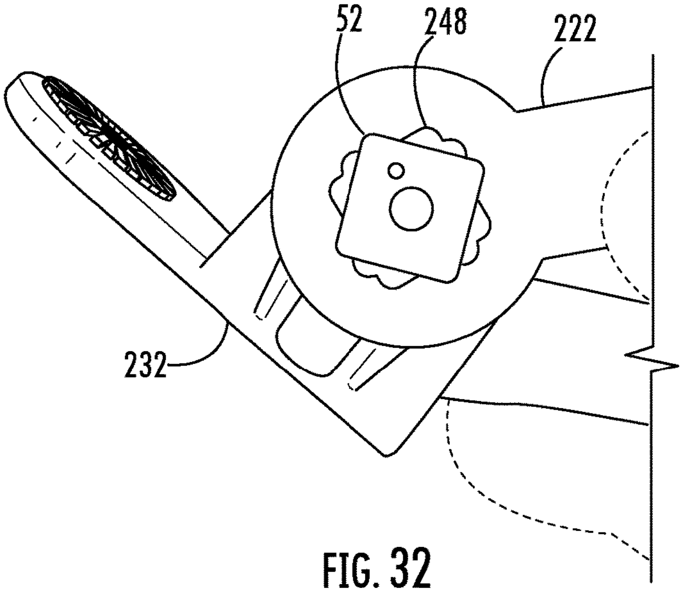
FIG. 32 is a bottom cutaway view of a spring clip and spring tensioner assembly attached to an end of a bar according to an aspect of the disclosure.
Figure 33:
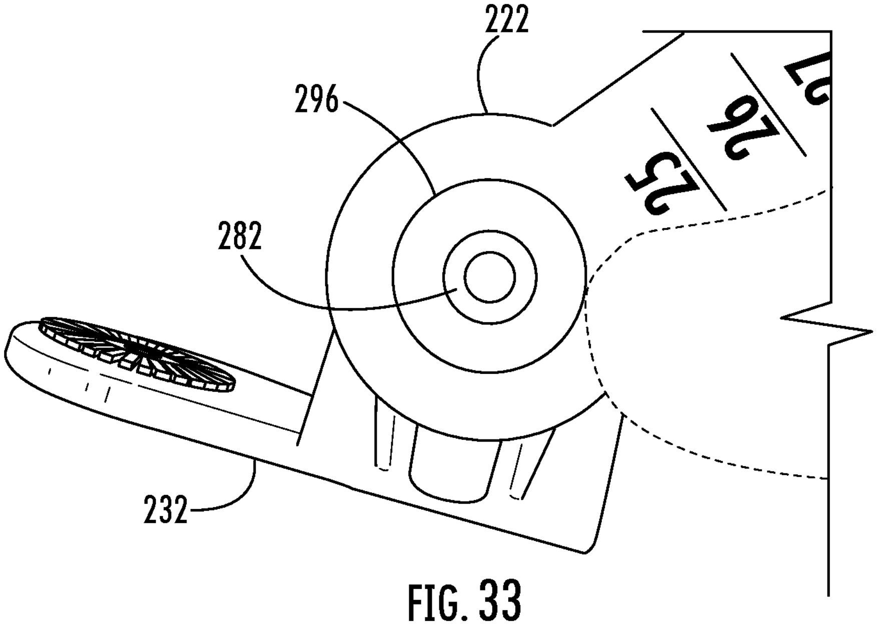
FIG. 33 is a bottom cutaway view of a spring clip and spring tensioner assembly attached to an end of the bar showing a washer of an aspect of the disclosure.

The anti-rotation hole 248 may be square, or as shown in FIG. 27 it may have a star-shape to allow for some adjustment in the orientation the spring arm 232 is attached to the bar 222. As shown in FIG. 31, the anti-rotation hole includes three positions for the square anti-rotation feature 52 on the inner insert housing 262 that extends outwardly from the bottom of the cup 242 of the spring arm 232. It should be known that any amount of positions or shapes may be cut to form the anti-rotation hole 248 as long as enough material of the bar remains to provide the resistance to prevent relative movement between the inner insert housing 262 and the bar 222.

Figure 34:
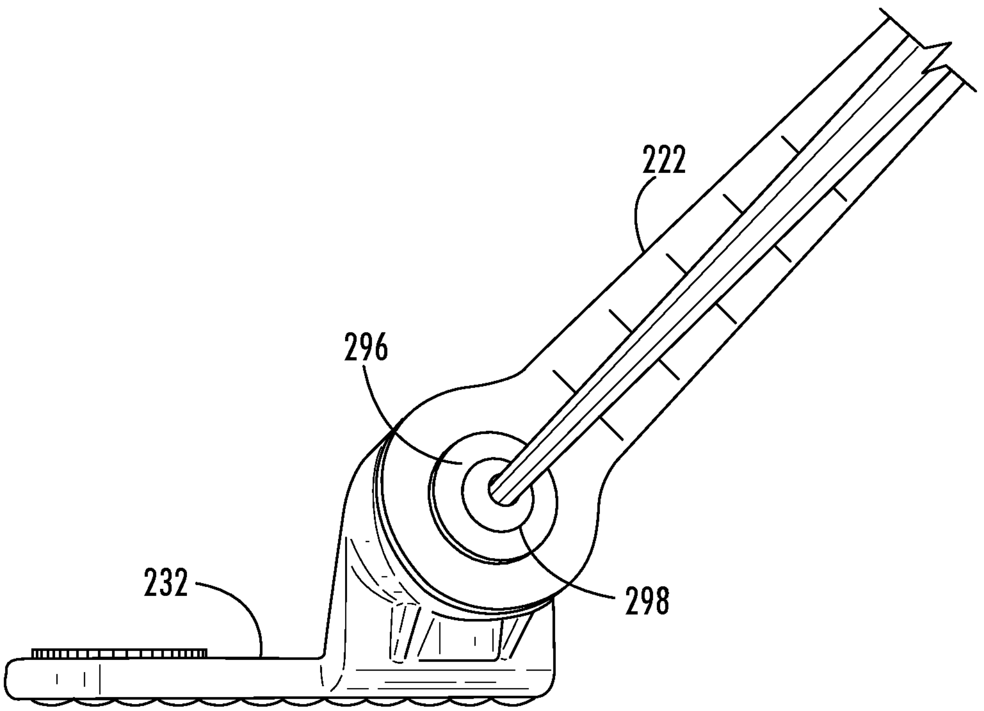
FIG. 34 is a bottom perspective view of a spring clip and spring tensioner assembly attached to an end of an orthotic bar showing the washer and fastener as the fastener is tightened into an engagement using a hex wrench of an aspect of the disclosure.
Figure 35:
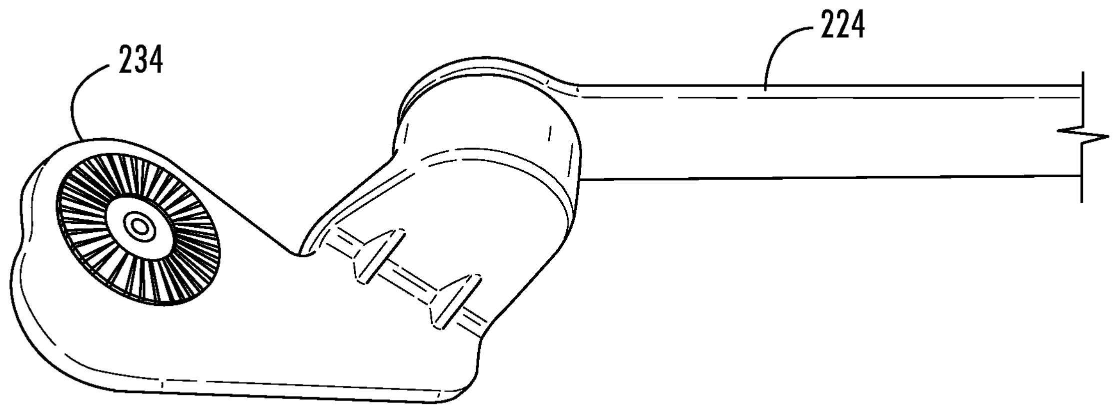
FIG. 35 is a top perspective view of a left bar assembly with a spring clip attached to the left bar according to an aspect of the disclosure.

Once the spring arm 232 is placed in the desired orientation on the bar 222, a washer 296 is placed over the center of a threaded hole 282 on the bottom side of the inner insert housing 262. A fastener 298 is then threaded and tightened into the hole 282, holding the spring arm 232 to the bar. As shown in FIG. 34, the fastener may be a button hex-head drive and may be tightened by a hex wrench, but it should be known that any type of fastener may be used. It should also be known that the hole 282 may be unthreaded, and the fastener may be a self-tapping fastener.

In the fourth stage of assembly shown in FIGS. 35-39B, the right bar 222 and left bar 224 are connected by a locking assembly 226. The locking assembly 26 receives the first bar 22 and the second bar 24 and holds them in place such that the ends 22*a*, 24*a* of bars 22, 24 are held at the proper, typically variable but predetermined, distance for a user and the user's specific clubfoot treatment. The right and left bars 222, 224 are placed one over another within the locking assembly 226. When the bars 222, 224 are set, a set screw may be placed within a threaded hole 227 and against the bars within the locking assembly 226, holding the bars in place at the desired length.

Figure 36:
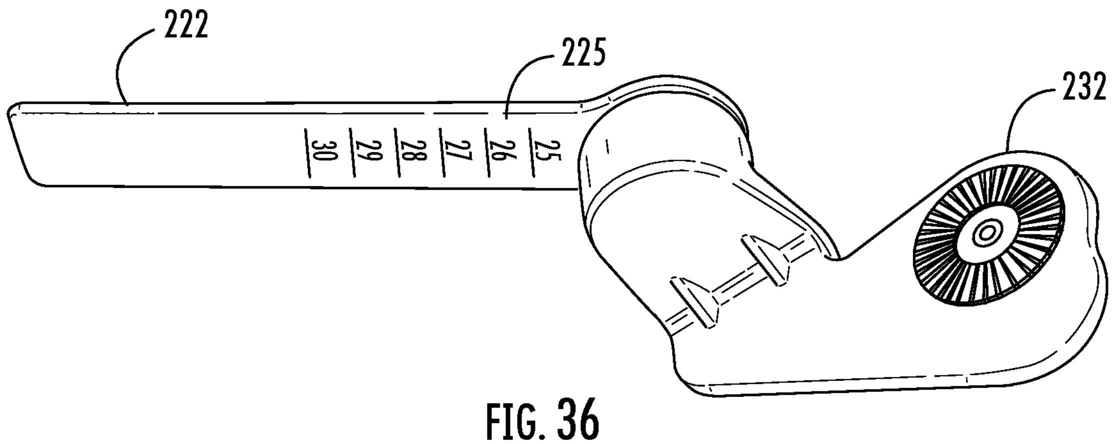
FIG. 36 is a top perspective view of a right bar assembly with the spring clip attached to the right bar having length markings according to an aspect of the disclosure.
Figure 37:
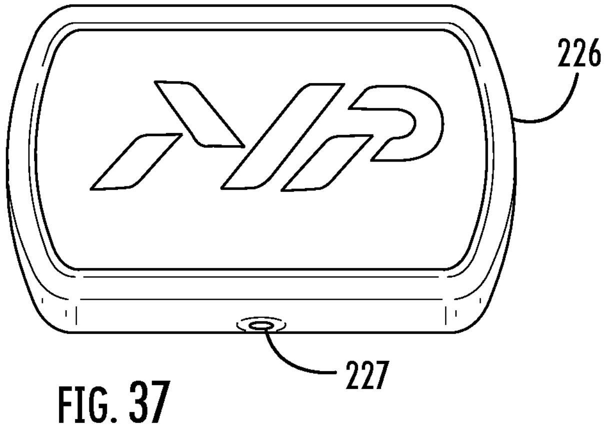
FIG. 37 is a top perspective view of a lock assembly according to an aspect of the disclosure.
Figure 38:
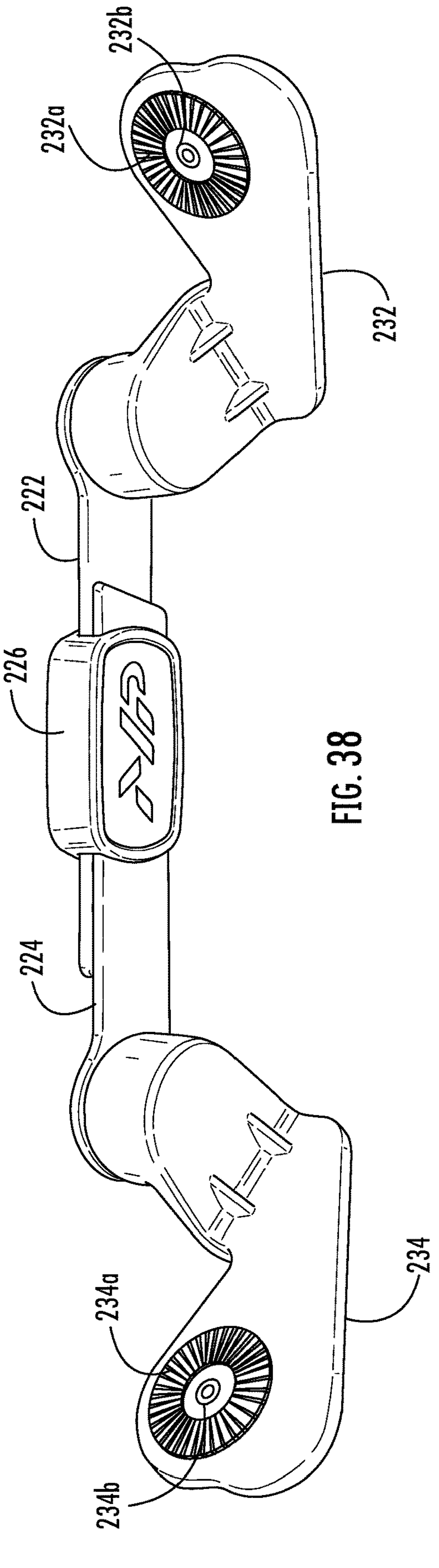
FIG. 38 is a top perspective view of an overall orthotic device in an assembled state according to an aspect of the disclosure.
Figure 39B:
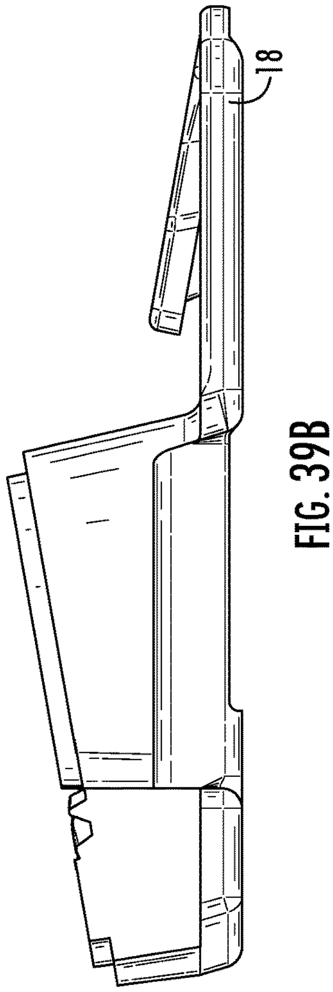
FIG. 39B is an elevated side view of the orthotic shoe clip shown in FIG. 39A where the clip has an angular top surface on the base and a clip extending away from the base at an angle as well.
Figure 39A:
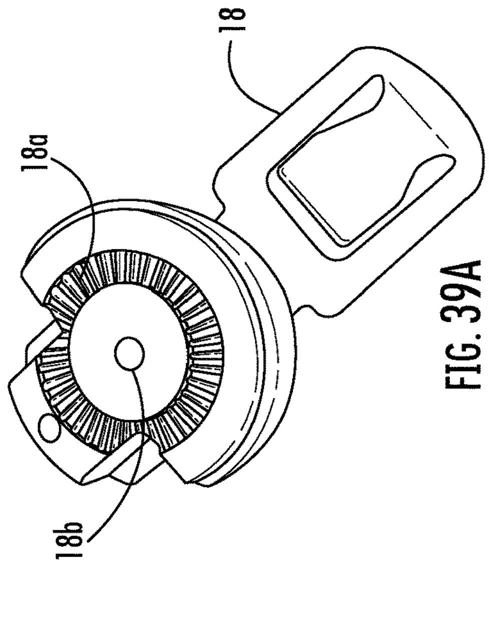
FIG. 39A is a top perspective view of a shoe clip according to an aspect of the disclosure.

One of the bars 222, 224 may include a number of length markings 225. As shown in FIG. 36, the right bar 222 includes the length markings 225 such that when the left bar 224 is placed over the top of the right bar 222 through the locking assembly 226, the end of the left 224 will read on the length markings 225 on the right bar 222. In this way a practitioner can easily and quickly set the desired length of the overall assembly for a given user.

With the length of the orthotic device 10 set, the practitioner may then attach the right and left quick connect clips 18, 20 to the right and left spring clips 232, 234. The right quick connect clip 18 shown in FIG. 39A and FIG. 39B includes a number of ribs 18*a* that correspond to ribs 232*a* on the right spring clip 232. Although not shown, the left quick connect clip 20 also includes a number of ribs 20*a* that correspond to ribs 234*a* on the left spring clip 234. In one embodiment, a common quick connect clip 18 is used on both the right and left spring clips 232, 234. The quick connect clip 18 is attached to the spring clip 232 (and quick connect clip 20 to spring clip 234) at the desired angle and a fastener is attached through hole 18*b* and into a threaded insert 232*b* holding the quick connect clip 18 to the spring clip 232. Ribs 18*a* interfere with ribs 232*a*, prevent the quick connect clip 18 from rotating with respect to the spring clip 232. The user may then attach the soles of their shoes to the quick connect clips to begin the treatment.

Figure 40:
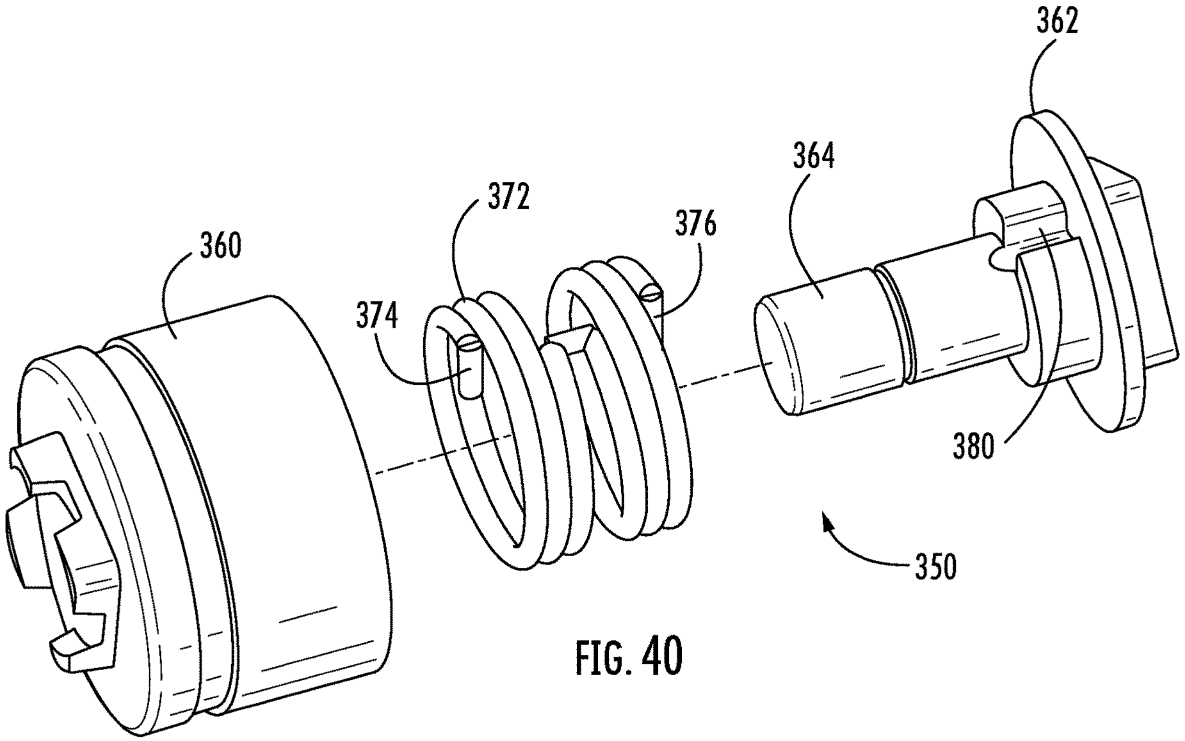
FIG. 40 is an exploded view of a spring tensioner according to another aspect of the disclosure with a torsion spring having two directions of coil.
Figure 41:
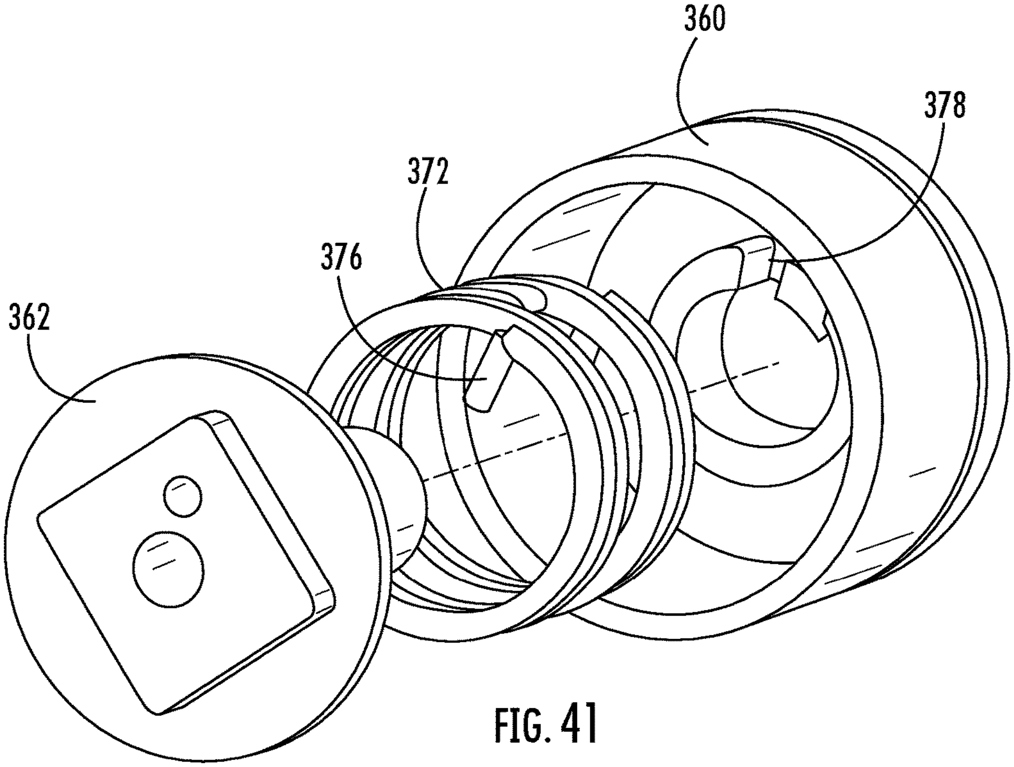
FIG. 41 is another exploded view of a spring tensioner of another aspect of the disclosure with a torsion spring having two directions of coil.
Figure 42:
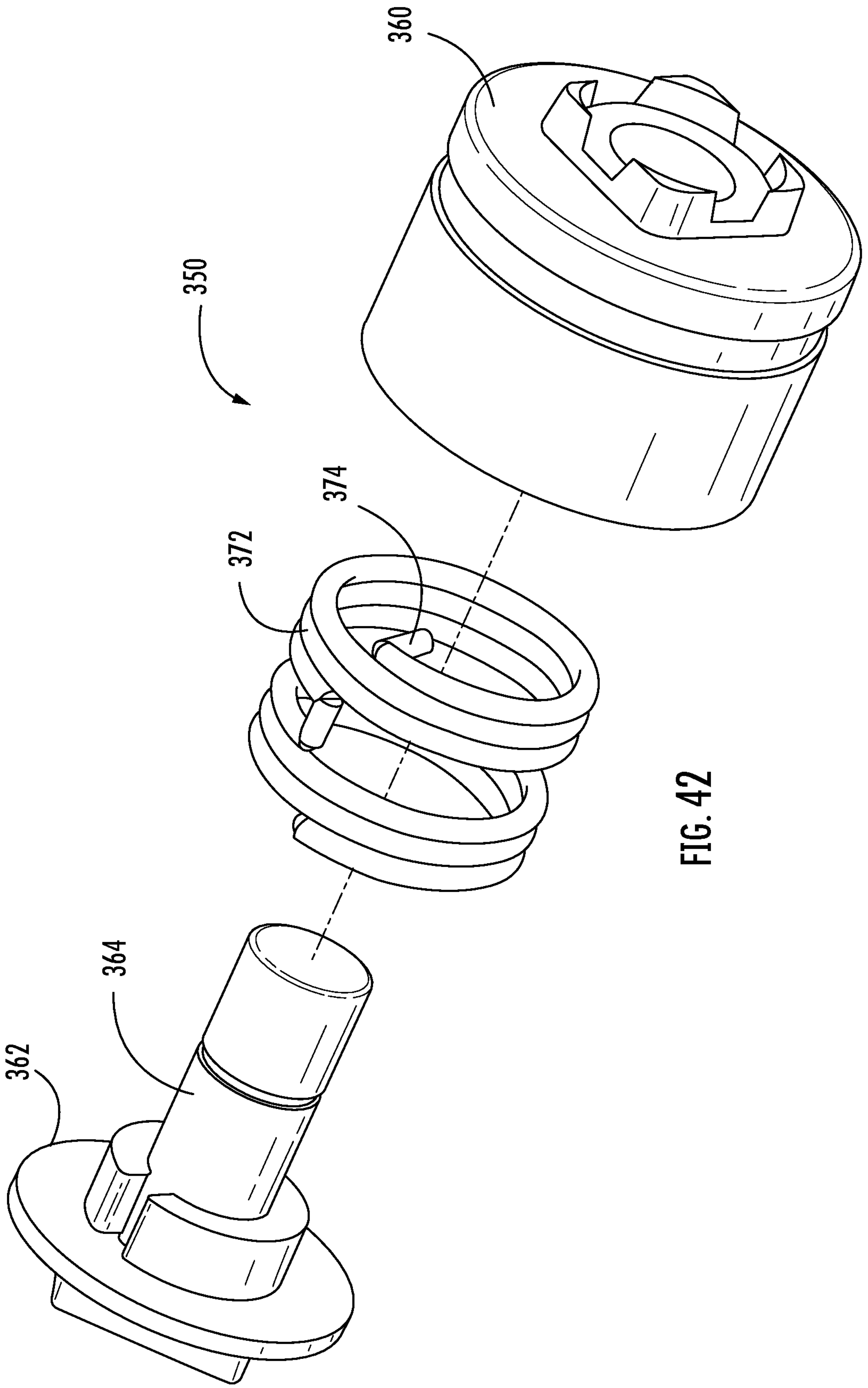
FIG. 42 is another exploded view of a spring tensioner of another aspect of the disclosure with a torsion spring having two directions of coil.
Figure 43:
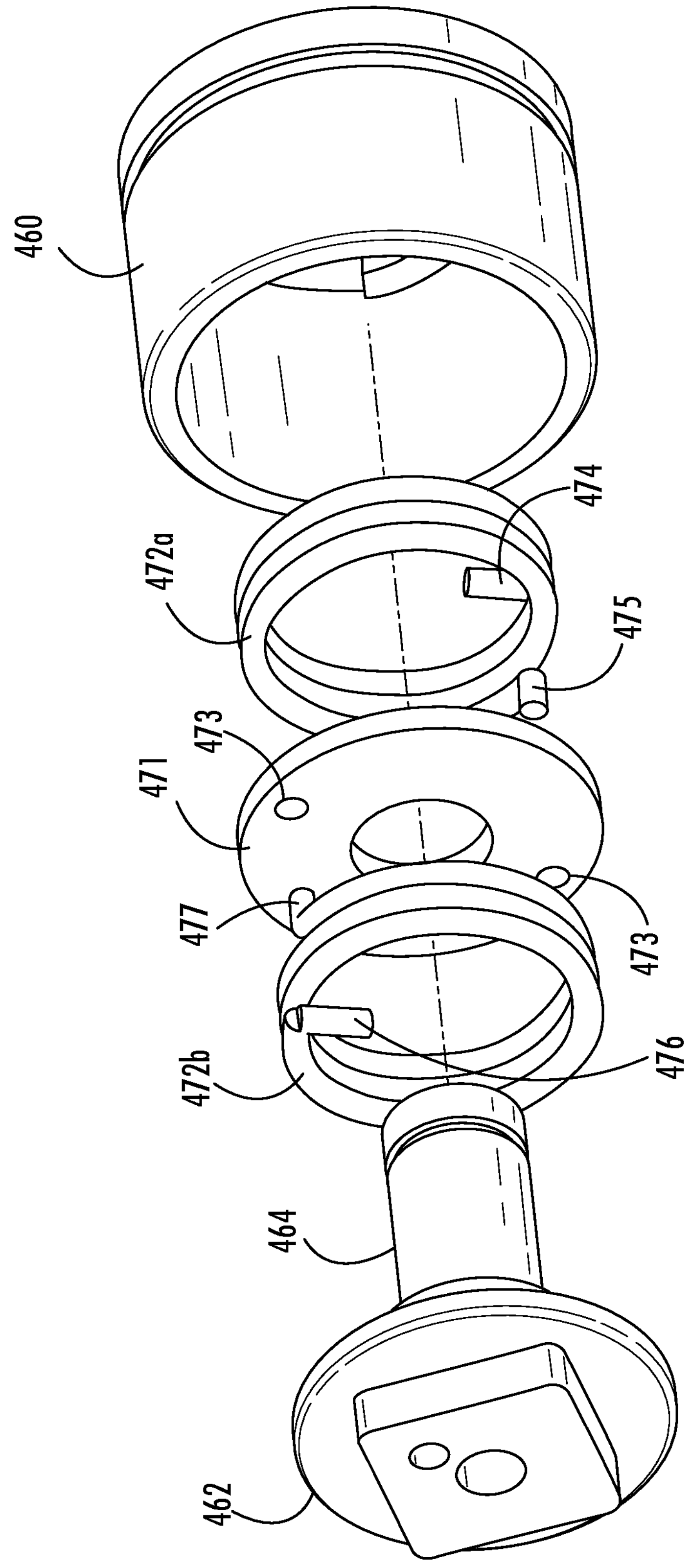
FIG. 43 is an exploded view of a spring tensioner of another aspect of the disclosure with two torsion springs having two directions of coil coupled by a spring disk.
Figure 44:
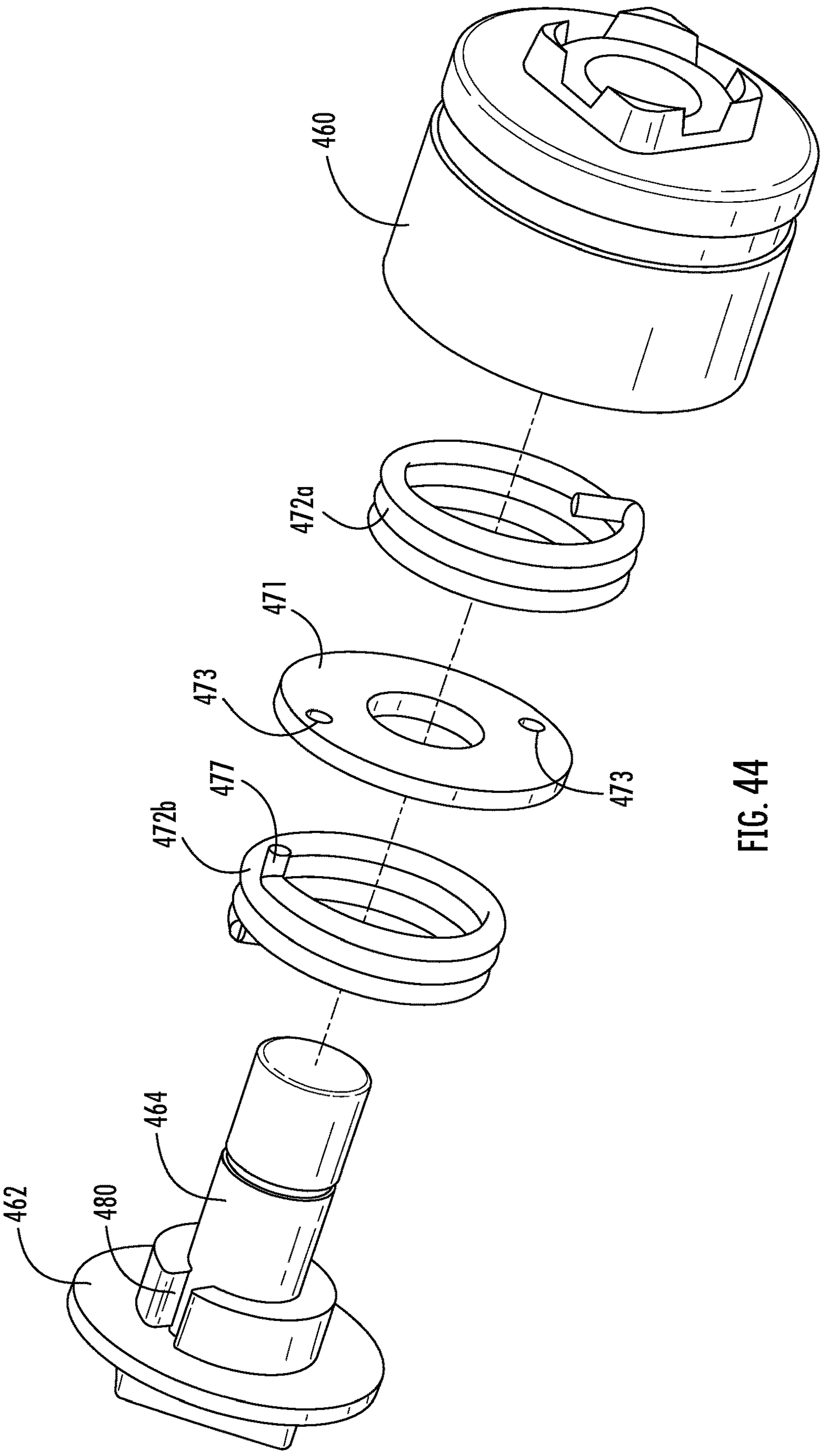
FIG. 44 is another exploded view of a spring tensioner of another aspect of the disclosure with two torsion springs having two directions of coil coupled by a spring disk.

Another embodiment of the spring tensioner 350 is shown in FIGS. 40-42, which is similar to spring tensioner 250 from FIGS. 11-18. The spring tensioner 350 includes an inner insert housing 362, an outer insert housing 360, and a spring 372, which may be a single two-way, one-piece spring, having ends 374, 376 that all assembled similarly as described above. In this case, as shown in the figures, the spring 372 is a single piece two-way coil spring that includes coil portions that go in either direction which allow for rotation and a return force in either direction that a user may twist their foot while using the orthotic device 10.

In still another embodiment of the spring tensioner 450, similar to the embodiments of spring tensioners 250 and 350, the spring tensioner 450 includes an inner insert housing 462 and an outer insert housing 460. The spring 472 further includes first and second springs 472*a* and 472*b*. Springs 472*a* and 472*b* may be similar springs or they may have opposite windings, they may have different numbers of coils, and/or may have different size gage such that the amount and direction of resistance may be finely tuned to a user's condition. The springs 472*a*, 472*b* may be coupled through a spring disk 471 having holes 473 and a center hole that allows the elongated post 464 extending from the cap of the inner insert housing 462 to pass through the center hole thereby anchoring the springs 472*a* and 472*b* relative to one another. The springs 472*a*, 472*b* include offshoots 475, 477 respectively, in addition to the offshoots 474 and 476 as described above. The offshoots 475, 477 mate with the holes 473 on the spring disk 471. Groove 480 receives and retains an end of the springs 472*b*.

It will be understood by one having ordinary skill in the art that construction of the described disclosure and other components is not limited to any specific material. Other exemplary embodiments of the disclosure disclosed herein may be formed from a wide variety of materials, unless described otherwise herein.

For purposes of this disclosure, the term "coupled" (in all of its forms, couple, coupling, coupled, etc.) generally means the joining of two components (electrical or mechanical) directly or indirectly to one another. Such joining may be stationary in nature or movable in nature. Such joining may be achieved with the two components (electrical or mechanical) and any additional intermediate members being integrally formed as a single unitary body with one another or with the two components. Such joining may be permanent in nature or may be removable or releasable in nature unless otherwise stated.

It is also important to note that the construction and arrangement of the elements of the disclosure as shown in the exemplary embodiments is illustrative only. Although only a few embodiments of the present innovations have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter recited. For example, elements shown as integrally formed may be constructed of multiple parts or elements shown as multiple parts may be integrally formed, the operation of the interfaces may be reversed or otherwise varied, the length or width of the structures and/or members or connector or other elements of the system may be varied, the nature or number of adjustment positions provided between the elements may be varied. It should be noted that the elements and/or assemblies of the system may be constructed from any of a wide variety of materials that provide sufficient strength or durability, in any of a wide variety of colors, textures, and combinations. Accordingly, all such modifications are intended to be included within the scope of the present innovations. Other substitutions, modifications, changes, and omissions may be made in the design, operating conditions, and arrangement of the desired and other exemplary embodiments without departing from the spirit of the present innovations.

It will be understood that any described processes or steps within described processes may be combined with other disclosed processes or steps to form structures within the scope of the present disclosure. The exemplary structures and processes disclosed herein are for illustrative purposes and are not to be construed as limiting.

It is also to be understood that variations and modifications can be made on the aforementioned structures and methods without departing from the concepts of the present disclosure, and further it is to be understood that such concepts are intended to be covered by the following claims unless these claims by their language expressly state otherwise.

What is claimed is:

1. A tensioning device system for an orthotic, comprising:

a first tensioning device, the first tensioning device including a cover having at least one wall extending upward from a base, an insert rotatably disposed within the cover, a slot within the at least one wall of the cover, a peg fixedly disposed on the insert and slidably located within the slot of the cover, the peg configured to slide between a first end portion and a second end portion of the slot, a spring fixedly attached to the cover and the insert such that the spring urges the cover and the insert in opposite rotational directions, a first flange surface on the cover, and a second flange surface on the insert and facing an opposite direction from the first flange surface, wherein the first flange surface and the second flange surface are operably coupled with third and fourth flange surfaces on an orthotic device to provide opposing forces on the tensioning device and wherein the tensioning device provides bias force when the cover is positioned to face upward or downward.

2. The tensioning device system of claim 1, further comprising:

a second tensioning device, the second tensioning device including a cover having at least one wall extending upward from a a base, an insert rotatably disposed within the cover, a slot within the at least one wall of the cover a peg fixedly disposed on the insert and slidably located within the slot of the cover, the peg configured to slide between a first end portion and a second end portion of the slot, a spring fixedly attached to the cover and the insert each that the spring urges the cover and the insert in opposite rotational directions, a first flange surface on the cover, and a second flange surface on the insert and facing an opposite direction from the first raised surface, wherein the first tensioning device has a first rotational tension, wherein the second tensioning device has a second rotational tension, and wherein the first flange surface and the second flange surface are operably coupled with third and fourth flange surfaces on an orthotic device to provide opposing forces on the tensioning device and wherein the tensioning device provides bias force when the cover is positioned to face upward or downward.

3. The tensioning device system of claim 2, wherein the cover of the first tensioning device has a first color, and the cover of the second tensioning device has a second color, the color of the first tensioning device and the color of the second tensioning device denoting the first tension and the second tension.

4. The tensioning device system of claim 2, wherein the cover of the first tensioning device has a first color, and the cover of the second tensioning device has a second color, the colors of the first tensioning device and the second tensioning device are configured to denote the first and second tensions of each of the first and second tensioning devices and wherein the first tensioning device is within a cavity formed by a portion of a first orthotic spring arm having a planar surface with an aperture therein and wherein the second tensioning device is within a cavity formed by a portion of a second orthotic spring arm and having a planar surface with an aperture therein.

5. The tensioning device system of claim 4, wherein a color of the insert and the color of the cover of the first tensioning device are the same.

6. The tensioning device system of claim 5, wherein a color of the insert and the color of the cover of the second tensioning device are the same.

7. The tensioning device system of claim 6, wherein the first flange surface mates with a torsion surface of one of an elongated bar and a shoe connection assembly.

8. The tensioning device system of claim 7, wherein the spring urges the peg toward the first end portion of the slot.

9. The tensioning device system of claim 6, further comprising:

an orthotic assembly including one of an elongated bar having a first torsion surface and a shoe connection assembly having a second torsion surface, wherein the second flange surface is configured to mate with one of the first torsion surface and the second torsion surface.

10. The tensioning device system of claim 1, further comprising:

an orthotic assembly including one of an elongated bar having a first torsion surface and a shoe connection assembly having a second torsion surface, wherein the second flange surface is configured to mate with one of the first torsion surface and the second torsion surface.

11. The tensioning device system of claim 1, wherein the spring urges the peg toward the first end portion of the slot.

12. A spring tensioner, comprising:

an outer insert housing having a center aperture, a stop peg, and a slot within an interior portion of the outer insert housing;

an inner insert housing comprising a center post configured to fit within and rotate within the center aperture of the outer insert housing, a slot, and two stop surfaces adjacent the post;

a coil spring with a first end and a second end, the first end of the coil spring disposed within the slot in the outer insert cover and the second end of the coil spring disposed within the slot in the inner insert housing;

wherein the inner insert housing is configured to rotate within the outer insert housing and wherein the stop peg of the outer insert housing is urged against a first of the two stop surfaces by the coil spring when the spring tensioner is in a default state, and wherein the peg is urged against a second of the two stop surfaces when a user twists the spring tensioner overcoming the coil force of the coil spring, a first flange surface on the outer insert housing;

a second flange surface on the inner insert housing and facing an opposite direction from the first flange surface; and wherein the first flange surface and the second flange surface are configured to operably couple with third and fourth flange surfaces on an orthotic device to provide opposing forces on the reversible tensioning device.

* * * * *